(12) United States Patent
Hassibi

(10) Patent No.: US 8,637,436 B2
(45) Date of Patent: Jan. 28, 2014

(54) INTEGRATED SEMICONDUCTOR BIOARRAY

(75) Inventor: Arjang Hassibi, Austin, TX (US)

(73) Assignee: California Institute of Technology, Pasadena, CA (US)

( * ) Notice: Subject to any disclaimer, the term of this patent is extended or adjusted under 35 U.S.C. 154(b) by 667 days.

(21) Appl. No.: 11/844,996

(22) Filed: Aug. 24, 2007

(65) Prior Publication Data

US 2008/0081769 A1 Apr. 3, 2008

Related U.S. Application Data

(60) Provisional application No. 60/840,060, filed on Aug. 24, 2006.

(51) Int. Cl.
*C40B 50/18* (2006.01)
*C40B 30/04* (2006.01)

(52) U.S. Cl.
USPC ............... 506/33; 506/16; 506/13; 257/255; 257/253; 530/350; 536/18.7

(58) Field of Classification Search
USPC ............... 506/33, 16, 13; 257/253, 255, 29; 530/350; 536/18.7
See application file for complete search history.

(56) References Cited

U.S. PATENT DOCUMENTS

| | | | |
|---|---|---|---|
| 5,599,668 A | 2/1997 | Stimpson et al. | |
| 7,463,353 B2 * | 12/2008 | Yershov | 356/317 |
| 7,599,060 B2 * | 10/2009 | Hoshizaki et al. | 356/317 |
| 7,630,227 B2 * | 12/2009 | Tran | 365/151 |
| 2007/0212681 A1 * | 9/2007 | Shapiro et al. | 435/5 |

OTHER PUBLICATIONS

Eltoukhy, et al. A 0.18-um CMOS bioluminescence detection lab-on-chip. Solid-State Circuits, IEEE Journal of: Mar 6, 2006; 41(3):651-662.
Hassibi, et al. A Programmable 0.18-$muhbox {m}$ CMOS Electrochemical Sensor Microarray for Biomolecular Detection. Sensors Journal, IEEE, Dec. 2006vol. 6, Issue: 6: 1380-1388.
Hassibi, et al. On noise processes and limits of performance in biosensors.J. Appl. Phys. 102, 014909 (2007) (12 pages).
McLeod. Thin-Film Optical Filters. 3rd Edition, Institute of Physics, London, 2001.
Parikh, et al. A CMOS Image Sensor for DNA Microarray, IEEE Custom Integrated Circuit Conf., 2007.
Schena. Microarray Analysis, Wiley, New York, 2003. (Table of Contents only).
Schienle, et al. A fully electronic DNA sensor with 128 positions and in-pixel A/D conversion. IEEE Journal of vol. 39, Issue 12, Dec. 2004 pp. 2438-2445.
Tolley, et al. Single-chain polymorphism analysis in long QT syndrome using planar waveguide fluorescent biosensors. Anal Biochem. Apr. 15, 2003;315(2):223-37.

\* cited by examiner

*Primary Examiner* — Teresa Wessendorf
(74) *Attorney, Agent, or Firm* — Milstein Zhang & Wu LLC; Joseph B. Milstein

(57) ABSTRACT

A biosensor array, system and method for affinity based assays that are able to simultaneously obtain high quality measurements of the binding characteristics of multiple analytes, and that are able to determine the amounts of those analytes in solution. The invention also provides a fully integrated bioarray for detecting real-time characteristics of affinity based assays.

30 Claims, 11 Drawing Sheets

INTEGRATED SEMICONDUCTOR BIOARRAY

CROSS-REFERENCE

This application claims priority to U.S. Provisional Application 60/840,060, filed Aug. 24, 2006, which is incorporated herein by reference in its entirety.

BACKGROUND OF THE INVENTION

Biosensor detection systems take advantage of the selective interaction and binding (affinity) of certain biological molecules to identify molecular structures and furthermore measure levels of different analytes such as toxins, polymers, hormones, DNA strands, proteins, and bacteria. Affinity-based biosensors exploit selective binding and interaction of certain bio-molecules (recognition probes) to detect specific target analytes in biological samples. The performance of biosensors in terms of signal to noise ratio and dynamic range is generally constrained by the characteristics of the molecular recognition layer which captures the target analytes, and not by the transducer and read-circuitry. An advantage of biosensors is their capability to be implemented in parallel and in an array format. Biosensors in parallel may compensate for limited detection performance. Presently, densely packed biosensor arrays which detect thousands of different analytes simultaneously (microarrays) are popular in Genomics, Proteomics, molecular diagnostics, and systems biology.

The essential role of the biosensor platforms and the parallel and miniaturized versions of them as microarrays are to exploit specific bindings of the probe-target complexes to produce detectable signals, which correlate with the presence of the targets and conceivably their abundance.

Many of the microarrays currently used in biological and medical research are DNA microarrays, in which the probe that is spotted or synthesized onto a solid surface is DNA. However, in addition to nucleic acids, microarray technologies are applicable to other types of biochemical compounds and analytes that can be immobilized on solid surfaces, such as proteins, carbohydrates, and lipids. Microarrays can be used to study the interactions between compounds of a same or different type (for example, protein-protein interactions, or protein-carbohydrate interactions).

Beside all the uncertainties within the measurement results, there is also a question in microarrays and most affinity-based biosensor systems, and that is of the necessary incubation time (hybridization time for DNA microarrays). Since the incubation kinetics in the microarrays experiments is a function of analyte diffusion, reaction chamber size, temperature and binding kinetics of every analyte species, as well as the unknown analyte concentrations, the settling time of the system is quite complex and unpredictable. Although all these questions can, to some extent, be empirically addressed, they are still major impediments in microarray technology and platform-to-platform inconsistencies can be caused by them.

In conventional fluorescent-based microarrays and other extrinsic reporter-based (label-based) biosensors assays, the detection of captured analytes is usually carried out after the incubation step. In some cases, proper fluorescent and reporter intensity measurements are compromised in the presence of a large concentration of floating (unbound) labeled species in the incubation solution, whose signal can overwhelm the target-specific signal from the captured targets. When the incubation is ceased and the solution is removed from the surface of the array, the washing artifacts often occur that make the analysis of the data even more challenging. Thus there exists a need for affinity based sensors that are able to simultaneously obtain high quality measurements of the binding characteristics of multiple analytes, and that are able to determine the amounts of those analytes in solution.

The emerging high-through screening and point-of-care (PoC) diagnostics applications demand the integration of the biochemical part (assays) of the detection platform with the transducer and the detection circuitry. A microarray is desired in the art that offers compact and cost-efficient solutions with a high production yield and robust functionality.

SUMMARY OF THE INVENTION

In an aspect of the invention, a biosensor array comprises, in order, a molecular recognition layer, an optical layer and a sensor layer integrated in a sandwich configuration. The molecular recognition layer can comprise an open surface and a plurality of different probes attached at different independently addressable locations to the open surface. The molecular recognition layer can transmit light to the optical layer. The optical layer comprises an optical filter layer, wherein the optical layer transmits light from the molecular recognition layer to the sensor layer. The sensor layer comprises an array of optical sensors that detect the filtered light transmitted through the optical layer.

In the biosensor array, the sensor layer can comprise embedded detection circuitry connected to the array of optical sensors. In another embodiment, the sensor layer comprises embedded detection and signal processing circuitry connected to the optical sensors.

The sensor layer can comprise a photodiode array.

In an embodiment, the sensor layer is a semiconductor device. The semiconductor device can be a silicon semiconductor device. Examples of a semiconductor device used as the sensor layer of an embodiment of the invention include, but are not limited to, a charge coupled device (CCD), a complementary metal oxide semiconductor (CMOS), and a digital signal processor.

In an embodiment, the biosensor array comprises an integrated in-pixel photocurrent detector. The detector can be capacitive transimpedance amplifier (CTIA).

In another embodiment, the biosensor array has an in-pixel analog to digital converter.

In an embodiment, the optical layer of the biosensor array further comprises an optical coupling layer between the optical filter layer and the molecular recognition layer. The optical coupling layer can comprise a plurality of optical waveguides. The optical coupling layer can also comprise a fiber-optic faceplate.

In an embodiment, the optical layer is 2 μm to 20 cm thick. In a further embodiment, the optical layer is 5 μm to 1 cm thick.

In another embodiment, the optical layer can provide thermal insulation between the sensor layer and the molecular recognition layer.

The optical filter layer of the optical layer can comprise a multilayer dielectric. In an embodiment, the optical filter has a passband or a stopband with a bandwidth of about 10 nm to 20 nm. In another embodiment, the passband or stopband is in the range of 400 nm to 800 nm.

In another embodiment, the optical filter attenuates fluorescent excitation light by $10^2$ to $10^7$. In a further embodiment, the optical filter attenuates fluorescent excitation light by $10^3$ to $10^5$.

The biosensor array can comprise at least one optical sensor corresponding to one independently addressable location comprising a probe. In another embodiment, more than one optical sensor corresponds to one independently addressable location. In yet another embodiment, about 10 to about 1000 optical sensors correspond to one independently addressable location. Different optical sensors corresponding to one independently addressable location can measure different wavelengths of light.

In an embodiment, the molecular recognition layer comprises 2 to 1,000,000 probes. The independently addressable regions of the molecular recognition layer can comprise probes comprising fluorescent moieties. In an embodiment, the fluorescent moieties are capable of being quenched upon binding of an analyte comprising a quencher. In another embodiment, the fluorescent moieties are bound to the probes. In yet another embodiment, the fluorescent moieties are bound to the surface of the array, but are not covalently bound to the probes.

In an embodiment, the probes comprise nucleic acids. In another embodiment, the probes comprise proteins.

In another aspect of the invention, a biosensor system comprises a fully integrated biosensor array comprising (a) a solid substrate comprising an array of semiconductor-based optical sensors, (b) an optical filter layer in contact with the solid substrate, (c) an optical coupling layer in contact with the optical filter layer, and (d) a molecular recognition layer in contact with the optical coupling layer and comprising a plurality of different probes, with different probes immobilized to the surface at a different addressable locations. The system further comprises a light source that directs light to the biosensor array, a fluidic chamber for holding fluid in contact with the biosensor array, a temperature controller for controlling the temperature of the fluid and/or the molecular recognition layer, and an interface that connects to the biosensor array to allow electronic communication to and from the array.

In an embodiment, the biosensor system further comprises a computer with software for process control and data collection and analysis. The system can comprise a plurality of biosensor arrays that use the same computer.

In an embodiment, the system comprises from 2 to 12 biosensor arrays.

In an embodiment, the different addressable locations of the fully integrated biosensor array comprise quenchable tags.

A system of the invention can comprise control circuitry that enables users to activate readout circuits and sensors on the array. In an embodiment, the system comprises control circuitry to specify temperature, mixing, fluorescent wavelength, fluorescent excitation power, pressure, and/or humidity. In another embodiment, at least part of the control circuitry is in the biosensor array.

In an embodiment, the system comprises decoder circuitry to select which of a plurality of sensors to be used. In a further embodiment, at least part of the decoder circuitry is in the biosensor array.

In an embodiment, the light source of the system is fixed, and illuminates all of the addressable locations.

In an aspect of the invention, a method comprises contacting a fluid containing a target analyte with a fully integrated biosensor array of the invention, illuminating the biosensor, detecting fluorescence on the biosensor, and correlating the detected fluorescence with binding of the target analyte.

In another aspect, a method comprises (a) contacting a fluid volume comprising a plurality of different analytes with a solid substrate comprising a plurality of different probes at independently addressable locations, wherein the probes are capable of specifically binding to the analytes, and (b) measuring signals at multiple time points while the fluid volume is in contact with the substrate, wherein the signals measured at multiple time points can be correlated with the amount of binding of the analytes with the probes. The solid substrate comprises an array of optical transducers, wherein at least one optical transducer correlates to one independently addressable location. In an embodiment, the method further comprises (c) using the signals measured at multiple time points to determine the concentration of an analyte in the fluid volume.

In an embodiment, a change in the signals with time correlates with the amount of the analytes bound to the probes.

In yet another aspect of the invention, a method comprises (a) performing a nucleic acid amplification on two or more nucleotide sequences to produce two or more amplicons in a fluid wherein the array comprises a solid surface with a plurality of nucleic acid probes at independently addressable locations. The solid substrate comprises an array of optical transducers, wherein at least one optical transducer correlates to one independently addressable location. The method also comprises (b) measuring the hybridization of the amplicons to the two or more nucleic acid probes while the fluid is in contact with the array to obtain an amplicon hybridization measurement. In an embodiment of the method of the invention, the method further comprises using the amplicon hybridization measurement to determine the concentration of the amplicons in the fluid. In another embodiment, the method further comprises using the amplicon hybridization measurement to determine the original amount of nucleotide sequences.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
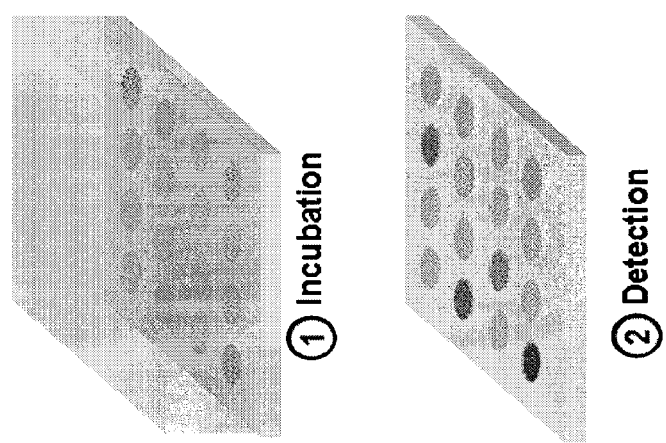
FIG. 1 illustrates an example of a conventional microarray of the prior art.

The devices, systems, and methods disclosed herein concern integrated biosensor arrays. One aspect of the invention is a fully integrated array which comprises a molecular recognition layer, an optical layer, and a sensor layer in a sandwich configuration. The biosensor array is capable of measuring the presence, amount, and binding characteristics of multiple analytes in solution by measuring the binding of the analytes to probes in the molecular recognition layer which is on an open surface of the biosensor array. The molecular recognition layer comprises a plurality of probes that are located on discrete, independently addressable regions. The optical layer comprises an optical filter layer such as a multilayer dielectric which selectively allows light within a given wavelength range to pass through to the sensor array. The optical layer can also comprise an optical coupling layer, for example a fiber optic faceplate that guides the light from the molecular layer to the optical filter layer and/or the sensor array. The sensor layer comprises an array of sensors, wherein typically the sensors correspond to the independently addressable regions of probes.

The sensor array can be a semiconductor based photodiode array which can be created in a silicon substrate using, for example, a CMOS process. Where the diode array is made by conventional silicon processing such as CMOS, additional circuitry can be incorporated into the array to enhance the signal processing capability of the array and to improve data quality. The additional circuitry can be incorporated into each pixel of the array, for example comprising an in-pixel photocurrent detector, or can be placed on other portions of the silicon chip. In some cases, the sensor array has multiple sensors, for example, 10 to 1000 sensors which correspond to the same independently addressable region of probe. In some cases, different sensors that correspond to the same addressable region of probe correspond to different regions of wavelength (different colors). The biosensor array could have a few addressable regions, such as 3 to 20, or could have a large number of addressable regions from 1,000 to 100,000 or more.

The biosensor arrays can be incorporated into a system comprising a light source for illuminating the sample, a fluidic chamber for holding the fluid in contact with the molecular recognition layer, a temperature controller for controlling hybridization conditions, an interface for allowing electronic communication with the array. The system can in some cases measure multiple biosensor arrays simultaneously.

The biosensor arrays of the present invention can be used for the detection of the binding of analytes in real-time. By measuring Real-time measurement of the kinetics of multiple binding events allows for an accurate and sensitive determination of binding characteristics or of analyte concentration for multiple species simultaneously. The abundance of target analytes in a sample can be evaluated by the real-time detection of target-probe binding events. In some embodiments, real-time microarray (RT-μArray) detection systems measure the concentration of the target analytes by analyzing the binding rates and/or the equilibrium concentration of the captured analytes in a single and/or plurality of spots. The measurement of analyte concentration during binding can avoid errors introduced in the washing and drying process used in many conventional microarrays. Measuring during binding also has the advantage of taking less time than waiting for saturation of binding before measuring analyte binding.

The molecular recognition layer can comprise fluorescent entities that are attached to the surface that are quenched by analytes comprising quenchers in solution. This method can be advantageous for measuring binding in the presence of solution because the analytes comprising quenchers can be designed so as to contribute minimally to background fluorescence. The fluorescent entities can be bound directly to the probe or can be bound to the surface in the vicinity of the probe.

The integrated biosensor arrays of the invention can be used to measure the concentration or binding characteristics of many types of probe-analyte binding pairs including proteins and nucleic acids. The measurement of nucleic acid hybridization on the biosensor arrays of the invention can be used to perform genomic and genetic expression analysis accurately and rapidly on many nucleotide sequences simultaneously. The biosensor arrays of the present invention can be used for accurate diagnostic and medical testing.

Biosensor Array

The biosensor array (bioarray) of the present invention is an integrated array comprising a molecular recognition layer, an optical layer, and a sensor layer.

A technique to measure the amount of captured analytes in microarrays (i.e., transduction method) is based on fluorescence spectroscopy. Previous microarray technology and biosensors have often been focused on systems with electrochemical transducers or partially integrated fluorescent and bioluminescence detectors. An example of a conventional microarray of the prior art is shown in FIG. 1. The system consists of an affinity-based assay located in contact with an array containing independently addressable probe locations. After a step of incubation to allow an analytes in the affinity-based assay to bind with an appropriate probe, the binding affinity can be detected by a sensor. Many systems of the prior art are two step systems as illustrated in FIG. 1.

Figure 2:
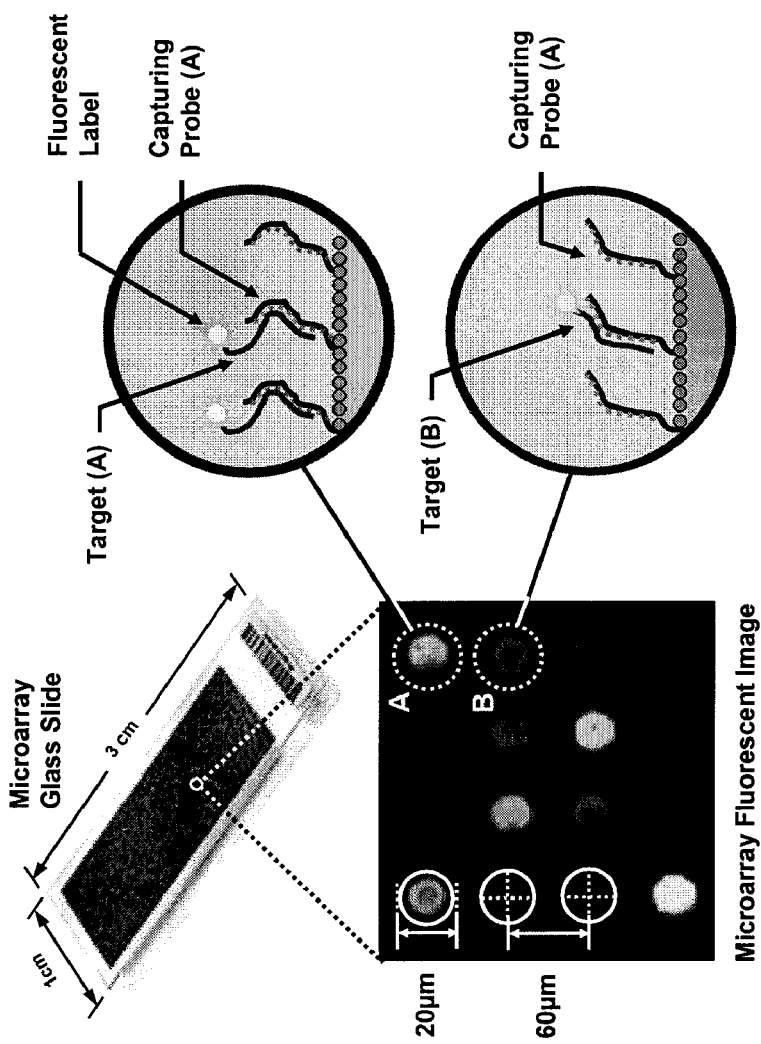
FIG. 2 displays an example of prior art microarray technology based upon fluorescent detection.

In many embodiments, the devices, systems, and methods of the invention utilize fluorescent detection. An example of prior art microarray technology based upon fluorescent detection is illustrated in FIG. 2. A microarray on a glass slide contains independently addressable locations containing capturing probes, as illustrated. A fluorescent label is attached to a target analyte. An incubation step is carried out to allow the target analyte to bind to the capturing probe. After the incubation step is complete, a fluorescent image can be taken of the microarray and the different independently addressable locations emit different signals corresponding to the amount of analyte bound on the location. In the present invention, the optical sensors are integrated into the substrate onto which capturing probes are bound.

An aspect of the invention is a fully integrated biosensor array comprising, in order, a molecular recognition layer, an optical layer and a sensor layer integrated in a sandwich configuration. The molecular recognition layer comprises an open surface and a plurality of different probes attached at different independently addressable locations to the open surface. The molecular recognition layer can also transmit light to the optical layer. The optical layer comprises an optical filter layer, wherein the optical layer transmits light from the molecular recognition layer to the sensor layer. The transmittal of light between layers can be filtered by the optical layer. The sensor layer comprises an array of optical sensors that detects the filtered light transmitted through the optical layer.

Figure 3:
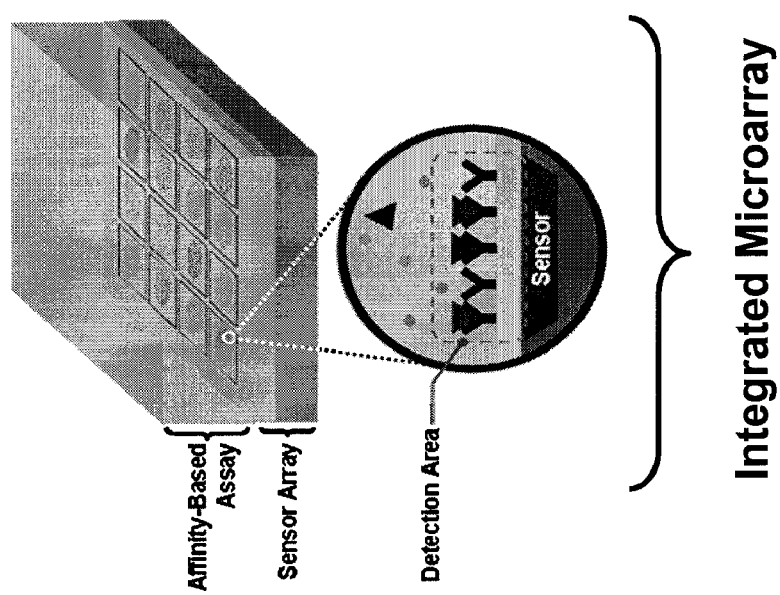
FIG. 3 illustrates an integrated biosensor array of the invention.

An integrated biosensor array of the invention can measure binding of analytes in real-time. FIG. 3 illustrates an embodiment of a device of the invention. An integrated biosensor microarray that can detect binding kinetics of an assay is in contact with an affinity-based assay. The biosensor array comprises a molecular recognition layer comprising binding probes in optical communication a sensor for detecting binding to the probes in real-time.

An integrated fluorescent-based microarray system for real-time measurement of the binding of analyte to a plurality of probes that includes the capturing probe layer, fluorescent emission filter, and image sensor can be built using a standard complementary metal-oxide semiconductor (CMOS) process.

The devices of the invention can measure binding of analytes to a plurality of probes on surface in "real-time". As used herein in reference to monitoring, measurements, or observations of binding of probes and analytes of this invention, the term "real-time" refers to measuring the status of a binding reaction while that reaction is occurring, either in the transient phase or in biochemical equilibrium. Real-time measurements are performed contemporaneously with the monitored, measured, or observed binding events, as opposed to measurements taken after a reaction. Thus, a "real-time" assay or measurement contains not only the measured and quantities result, such as fluorescence, but expresses this at various time points, that is, in hours, minutes, seconds, milliseconds, nanoseconds, etc. "Real-time" includes detection of the kinetic production of signal, comprising taking a plurality of readings in order to characterize the signal over a period of time. For example, a real-time measurement can comprise the determination of the rate of increase or decrease in the amount of analyte bound to probe.

Real-time measurement can include the measurement of the binding kinetics to characterize binding of multiple probes and analytes in solution. In some cases, binding reaction refers to the concurrent binding reactions of multiple analytes and probes, and in other cases, the term binding reaction refers to the reaction between a single probe with a single analyte. The meaning will be clear from the context of use. The kinetic measurements can be expressed as the amount of analyte bound to the probe as a function of time. The binding kinetics can provide information about the characteristics of the probe-analyte binding such as the strength of binding, the concentration of analyte, the competitive binding of an analyte, the density of the probes, or the existence and amount of cross-hybridization.

In order to determine binding kinetics, the signal at multiple time points must be determined. The signal at least two time points is required. In most cases, more than two time points will be desired in order to improve the quality of the kinetic information. In some embodiments the signal at, 2-10, 10-50, 50-100, 100-200, 200-400, 400-800, 800-1600, 1600-3200, 3200-6400, 6400-13000, or higher than 13,000 time points will be measured. One of ordinary skill in the art can determine the effective number of points for a given embodiment.

The frequency at which the signal is measured will depend on the kinetics of the binding reaction or reactions that are being monitored. As the frequency of measurements gets lower, the time between measurements gets longer. One way to characterize a binding reaction is to refer to the time at which half of the analyte will be bound ($t_{1/2}$). The binding reactions of the invention can have a ($t_{1/2}$) from on the order of milliseconds to on the order of hours, thus the frequency of measurements can vary by a wide range. The time between measurements will generally not be even over the time of the binding reaction. In some embodiments, a short time between of measurements will be made at the onset of the reaction, and the time between measurements will be longer toward the end of the reaction. One advantage of the present invention is the ability to measure a wide range of binding rates. A high initial frequency of measurements allows the characterization of fast binding reactions which may have higher binding, and lower frequency of measurements allows the characterization of slower binding reactions. For example, points can initially be measured at a time between points on the order of a microsecond, then after about a millisecond, points can be measured at a time between points on the order of a millisecond, then after about a second, time points can be measured at a time between points on the order of a second. Any function can be used to ramp the change in measurement frequency with time. In some cases, changes in the reaction conditions, such as stringency or temperature changes will be made during a reaction, after which it may be desirable to change the frequency of measurements to measure the rates of reaction which will be changed by the change in reaction condition.

In some embodiments, a probe will have substantially no analyte bound to it at the beginning of the binding reaction, then the probe will be exposed to a solution containing the analyte, and the analyte will begin to bind, with more analyte bound to the probe with time. In some cases, the reaction will reach saturation, the point at which all of the analyte that is going to bind has bound. Generally, saturation will occur when a reaction has reached steady state. At steady state, in a given time period, just as many analytes are released as new analytes are bound (the on rate and off rate are equal). In some cases, with very strong binding, where the off-rate for the analyte is essentially zero, saturation will occur when substantially all of the analyte that can bind to the probe will have bound, has bound. Thus, while it is advantageous to measure a change in signal with time that can be correlated with binding kinetics, the measurement of a signal that does not change with time also provides information in the context of a real-time experiment, and can also be useful in the present invention. For example, in some cases the absence of a change in the signal will indicate the level of saturation. In other cases the absence of a change in signal can indicate that the rate of the reaction is very slow with respect to the change in time measured. It is thus a beneficial aspect of this invention to measure binding event in real time both where signals change with time and where the signals do not change with time.

One aspect of the methods of the present invention is the measurement of concentration of an analyte from the measurement of binding kinetics. Since analyte binding rate can be concentration-dependant, we can estimate the analyte abundance in the sample solution using binding rates.

One aspect of the present invention is the determination of the binding of analyte to probe by measuring the rate near the beginning of the reaction. In addition to providing a more reliable estimate of C, measurement near the beginning of the reaction can shorten the time that is required to measure analyte binding over the time required for measuring binding from saturation. In some embodiments of the invention, the binding is measured during the time for less than about the first 0.1, 0.5, 1, 2, 3, 4, 5, 6, 8, 10, 12, 14, 18, 20, 25, 30, 40, 50, 60, 70, 80, or 90 percent of the analyte to bind as compared to the amount of analyte bound at saturation. In some embodiments, the binding kinetics are determined in a time for less than about the first 20% of the analyte to bind. In some embodiments, the binding kinetics are determined in a time for less than about the first 1-2% of the analyte to bind.

Molecular Recognition Layer

A molecular recognition layer of the present invention comprises an open surface of the biosensor array.

A molecular recognition layer of the invention comprises a plurality of probes located at independently addressable locations for detecting different analytes. The probes can specifically bind with analytes in solution in order to determine the concentration and binding characteristics of the analytes. The probes can be used to detect analytes including, but not limited to, polymers, hormones, DNA strands, proteins, and bacteria. In some embodiments, the molecular recognition layer comprises 2 to 1,000,000 probes.

In another embodiment, the independently addressable regions comprise probes that are fluorescent moieties. The fluorescent moieties can also be bound to the probes. The probe-bound fluorescent moieties can be quenched by analytes comprising quenchers, such that the quenching of fluorescence can be used to determine the concentration of analyte in solution. The molecular recognition layer can transmit light through an optical layer to a sensor layer in a biosensor array of the invention. Often, the light is transmitted by fluorescence from the interaction and binding of an analyte to a probe through the optical layer to the sensor layer.

In some embodiments, the fluorescent moieties are bound to the surface of the array, and are not covalently bound to the probes. Surface bound fluorescent moieties can be quenched by analytes in solution comprising quenchers and thus used to determine the concentration of analyte in solution even where the fluorescent moiety is not bound to the probe itself.

In an embodiment, the probes of the molecular recognition layer are nucleic acids. The probes can also be proteins.

In other embodiments, the RT-µArray is placed onto a transducer array. The distance of the probes to the transducer array in such a setup can be from 1 mm to 0.1 µm. In some embodiments, the distance is about 20 µm to 2 µm.

The arrays of the present invention comprise probes which comprise a molecular recognition layer. The layer may be biological, nonbiological, organic, inorganic, or a combination of any of these. The surface on which the probes reside can exist as particles, strands, precipitates, gels, sheets, tubing, spheres, containers, capillaries, pads, slices, films, plates, slides, semiconductor integrated chips, etc. The surface is preferably flat but may take on alternative surface configurations. For example, the molecular recognition layer may occur on raised or depressed regions on which synthesis or deposition takes place. In some embodiments, the molecular recognition layer will be chosen to provide appropriate light-absorbing characteristics. For example, the layer may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidenedifluoride, polystyrene, polycarbonate, or combinations thereof.

The surface can be a homogeneous solid and/or unmoving mass much larger than the capturing probe where the capturing probes are confined and/or immobilized within a certain distance of it. In certain embodiments, the surface is planar with roughness of 0.1 nm to 100 nm, but typically between 1 nm to 10 nm. In other embodiments the surface can be a porous surface with roughness of larger than 100 nm. In other embodiments, the surface can be non-planar. Examples of non-planar surfaces are spherical magnetic beads, spherical glass beads, and solid metal and/or semiconductor and/or dielectric particles.

The molecular recognition layer is typically in contact with fluid that is optically transparent to an excitation source light. After excitation of the molecular recognition layer, the layer can emit an optical wavelength that can be detected.

In some embodiments, the molecular recognition layer may be bound to a glass surface when the optical layer comprises glass. The molecular recognition layer can also be bound to silica, silicon, plastic, metal, metal-alloy, anopore, polymeric, and nylon. The surfaces to which the molecular recognition layer is bound can be treated with a layer of chemicals prior to attaching probes to enhance the binding or to inhibit non-specific binding during use. For example, glass surfaces can be coated with self-assembled monolayer (SAM) coatings, such as coatings of as aminoalkyl silanes, or of polymeric materials, such as acrylamide and proteins.

Probes can be attached covalently (but non-covalent attachment methods can also be used). A number of different chemical surface modifiers can be added to the surface to attach the probes. Examples of chemical surface modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. Glass slides with such chemically modified surfaces are commercially available for a number of modifications. These can easily be prepared for the rest, using standard methods (Microarray Biochip Technologies, Mark Schena, Editor, March 2000, Biotechniques Books).

In some embodiments, surfaces that are reactive to probes comprising amines are used. An advantage of this reaction is that it is fast, with no toxic by-products. Examples of such surfaces include NHS-esters, aldehyde, epoxide, acyl halide, and thio-ester. Most proteins, peptides, glycopeptides, etc. have free amine groups, which will react with such surfaces to link them covalently to these surfaces. Nucleic acid probes with internal or terminal amine groups can also be synthesized, and are commercially available (e.g., from IDT or Operon). Thus, nucleic acids can be bound (e.g., covalently or non-covalently) to surfaces using similar chemistries.

The surfaces to which the probes are bound need not be reactive towards amines, but can be easily converted into amine-reactive surfaces with coatings. Examples of coatings include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), and BSA coatings (which can be reacted with bis-NHS cross-linkers, maleimide-NHS cross-linkers, etc.). Alternatively, the probes, rather than the open surface, can be reacted with specific chemical modifiers to make them reactive to the respective surfaces.

A number of other multi-functional cross-linking agents can be used to convert the chemical reactivity of one kind of surface to another. These groups can be bifunctional, tri-functional, tetra-functional, and so on. They can also be homo-functional or hetero-functional. An example of a bi-functional cross-linker is X—Y—Z, where X and Z are two reactive groups, and Y is a connecting linker. Further, if X and Z are the same group, such as NHS-esters, the resulting cross-linker, NHS—Y—NHS, is a homo-bi-functional cross-linker and would connect an amine surface with an amine-group containing molecule. If X is NHS-ester and Z is a maleimide group, the resulting cross-linker, NHS—Y-maleimide, is a hetero-bi-functional cross-linker and would link an amine surface (or a thiol surface) with a thio-group (or amino-group) containing probe. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc. Such cross-linkers can be reacted with the surface or with the probes or with both, in order to conjugate a probe to a surface.

Other alternatives include thiol reactive surfaces such as acrydite, maleimide, acyl halide and thio-ester surfaces. Such surfaces can covalently link proteins, peptides, glycopeptides, etc., via a (usually present) thiol group. Nucleic acid probes containing pendant thiol-groups can also be easily synthesized.

Alternatively, one can modify glass surfaces with molecules such as polyethylene glycol (PEG), e.g. PEGs of mixed lengths.

Other surface modification alternatives (such as photocrosslinkable surfaces and thermally cross-linkable surfaces) are known to those skilled in the art. Some technologies are commercially available, such as those from Mosiac Technologies (Waltham, Mass.), Exiqon™ (Vedbaek, Denmark), Schleicher and Schuell (Keene, N. H.), Surmodics™ (St. Paul, Minn.), Xenopore™ (Hawthorne, N. J.), Pamgene (Netherlands), Eppendorf (Germany), Prolinx (Bothell, Wash.), Spectral Genomics (Houston, Tex.), and Combimatrix™ (Bothell, Wash.).

Surfaces other than glass are also suitable binding the probes of the molecular recognition layer. For example, metallic surfaces, such as gold, silicon, copper, titanium, and aluminum, metal oxides, such as silicon oxide, titanium oxide, and iron oxide, and plastics, such as polystyrene, and polyethylene, zeolites, and other materials can also be used. In some embodiments, the layers of these materials will have to be made thin, e.g. less than about 100 nm in order to allow the transmission of light. The devices can also be prepared on LED (Light Emitting Diode) and OLED (Organic Light Emitting Diode) surfaces. An array of LEDs or OLEDs can be used at the base of a probe array. An advantage of such systems is that they provide easy optoelectronic means of result readout. In some cases, the results can be read-out using a naked eye.

Probes can be deposited onto the substrates, e.g., onto a modified surface, using either contact-mode printing methods using solid pins, quill-pins, ink-jet systems, ring-and-pin systems, etc. (see, e.g., U.S. Pat. Nos. 6,083,763 and 6,110, 426) or non-contact printing methods (using piezoelectric, bubble-jet, syringe, electro-kinetic, mechanical, or acoustic methods. Devices to deposit and distribute probes onto substrate surfaces are produced by, e.g., Packard Instruments. There are many other methods known in the art. Preferred devices for depositing, e.g., spotting, probes onto substrates include solid pins or quill pins (Telechem/Biorobotics).

In other embodiments, the molecular recognition layer is manufactured through the in-situ synthesis of the probes. This in-situ synthesis can be achieved using phosphoramidite chemistry and/or combinatorial chemistry. In some cases, the deprotection steps are performed by photodeprotection (such as the Maskless Array Synthesizer (MAS) technology, (NimbleGen, or the photolithographic process, by Affymetrix). In other cases, deprotection can be achieved electrochemically (such as in the Combimatrix procedure). Microarrays for the present invention can also be manufactured by using the inkjet technology (Agilent).

For the arrays of the present invention, the plurality of probes may be located in one addressable region and/or in multiple addressable regions on the open surface of the molecular recognition layer. In some embodiments the molecular recognition layer has about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 addressable regions with probes.

The spots may range in size from about 1 nm to about 10 mm, in some embodiments from about 1 to about 1000 micron and more in some embodiments from about 5 to about 100 micron. The density of the spots may also vary, where the density is generally at in some embodiments about 1 spot/$cm^2$, in some embodiments at least about 100 spots/$cm^2$ and in other embodiments at least about 400 spots/$cm^2$, where the density may be as high as $10^6$ spots/$cm^2$ or higher.

The shape of the spots can be square, round, oval or any other arbitrary shape.

In some embodiments it is also useful to have addressable regions which do not contain probe, for example, to act as control spots in order to increase the quality of the measurement, for example, by using binding to the spot to estimate and correct for non-specific binding.

Sensor Layer

The sensor layer comprises an array of optical sensors. The sensor array detects the light that is transmitted at the molecular recognition layer. The light that reaches the sensor array will have passed through the optical layer which comprises an optical filter layer that only allows a portion of the spectrum of light and/or certain wavelengths to reach the sensors.

The array of optical sensors can be utilized to detect analyte interaction and binding on the molecular recognition layer by receiving information from an emitted fluorescent signal. An optical sensor of the sensor layer can be positioned to correspond with each independently addressable location of the molecular recognition layer. In an embodiment, at least one or more optical sensors of the sensor layer correspond to a probe or set of probes. In an embodiment, 1 optical sensor corresponds to one independently addressable location. In another embodiment, 10-1000 optical sensors correspond to one independently addressable location. In a further embodiment, different optical sensors corresponding to the one independently addressable location measure different wavelengths of light.

In an embodiment of the invention, the array of optical sensors of the sensor layer is a part of a semiconductor based sensor array. The semiconductor based sensor array can be either an organic semiconductor or an inorganic semiconductor. In some embodiments, the semiconductor device is a silicon-based sensor. Examples of sensors useful in the present invention include, but are not limited to, a charge-coupled device (CCD), a CMOS device, and a digital signal processor. The semiconductor device of the sensor layer can also comprise an integrated in-pixel photocurrent detector. The detector may comprise a capacitive transimpedance amplifier (CTIA).

In another embodiment, the semiconductor device has an in-pixel analog to digital converter.

In another embodiment, the array of optical sensors of the sensor layer can be a photodiode array.

The sensor layer can be created using a CMOS process. A semiconductor detection platform can be the assembly of an integrated system capable of measuring the binding events of real-time microarrays (RT-µArrays). In some embodiments, an integrated device system involves a transducer array that is placed in contact with or proximity of the RT-µArray assay.

A semiconductor detection platform for RT-µArrays can include an array of independent transducers to receive and/or analyze the signal from target and probe binding events of a RT-µArray platform. A plurality of transducers can work collectively to measure a number of binding events at any individual microarray spot. For example, transducers dedicated to a spot may add and/or average their individual measured signal.

Detection circuitry connected to an array of optical sensors can be embedded in the sensor layer. Signal processing circuitry can also be connected to the array of optical sensors and embedded in the sensor layer. In some embodiments, the transducers and/or detection circuitry and/or analysis systems are implemented using electronic components which are fabricated and/or embedded in the semiconductor substrate. Examples of such fabrication techniques include, but are not limited to, silicon fabrication processes, micro-electromechanical surface micromachining, CMOS fabrication processes, CCD fabrication processes, silicon-based bipolar fabrication processes, and gallium-arsenide fabrication processes.

The transducer array can be an image sensor array. Examples of such image arrays include, but are not limited to, CMOS image sensor arrays, CMOS linear optical sensors, CCD image sensors, and CCD linear optical sensors. The image sensor can be used to detect the activity of the probe/analyte interaction within the integrated biosensor array platform.

Figure 4:
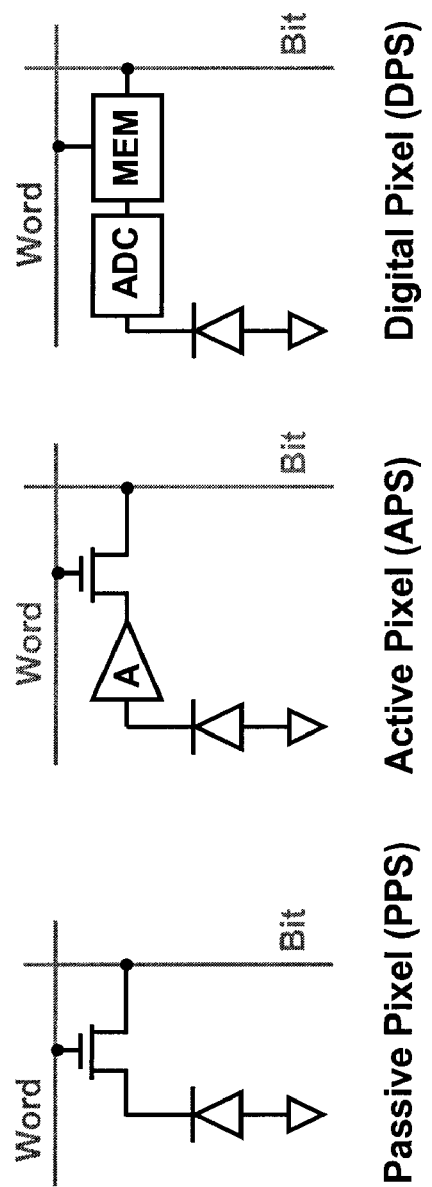
FIG. 4 demonstrates a passive pixel sensor (PPS), an active pixel sensor (APS), and a digital pixel sensor (DPS) for use as the pixel architecture of a CMOS image sensor array.

The pixel architecture within the CMOS image sensor array can be passive pixel sensor (PPS), active pixel sensor (APS) or digital pixel sensor (DPS) as illustrated in FIG. 4. In all these architectures the light in converted to current using an integrated photodiode. The current in PPS is directly read from the photodiode by selecting the associated word and bit lines, while in APS architecture the current is initially integrated and converted to voltage and then is read. In DPS and analog-to-digital converter digitizes the read signal making the pixel output digital as opposed to analog in PPS and APS.

As used herein, the terms detector and transducer are used interchangeably, and refer to a component that is capable of detecting a signal that can be correlated with an value of analyte/probe binding.

In some embodiments the detector array is in contact with the molecular recognition layer. In some embodiments, the detector is spaced from the molecular recognition layer. The detector can be optically coupled to the molecular recognition layer, for example, with one or more lenses or waveguides.

Figure 5:
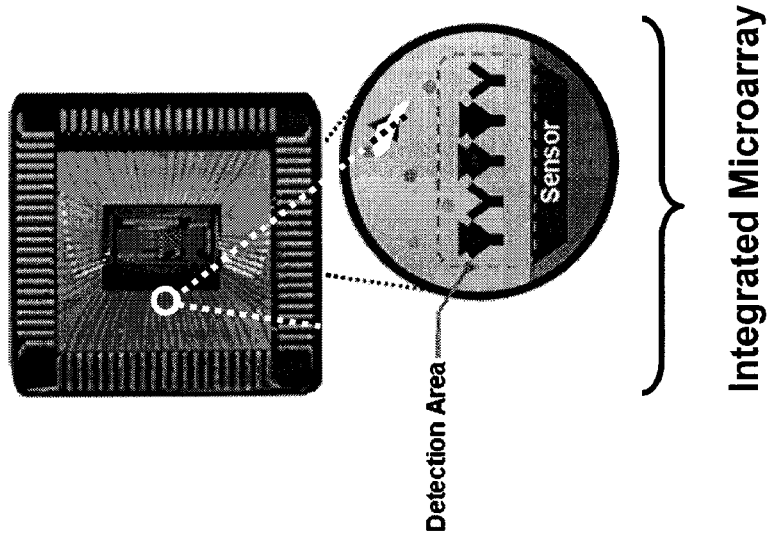
FIG. 5 shows an example of a CMOS embodiment of the present invention.

FIG. 5 shows an example of a CMOS embodiment of the present invention. A semiconductor is utilized as a sensor for detecting the binding of the molecular recognition layer, or in this example, the detection area. The detection area is located on the device in a layer separated from the sensor layer by an optical layer.

In some embodiments, the detector is optically coupled through imaging using focal plane detector arrays: In this method the signal generated from the system is focused on a focal point detector array. This approach useful for optical detection systems where signal focusing can be carried out using lenses and other optical apparatus. Examples of detectors in these embodiments are CMOS and CCD image sensors.

Detectors can be placed such that the signal generated from the capturing region can only be observed by the dedicated detector. If a microarray with multiple capturing spots is used, multiple detectors are used, each dedicated to an individual spot.

The detectors of the present invention are generally capable of capturing signal at multiple time points in real-time, during the binding reaction. In some embodiments the detector is capable of measuring at least two signals in less than about 1 psec, 5 psec, 0.1 nsec, 0.05 nsec, 0.1 nsec, 0.5 nsec, 1 nsec, 5 nsec, 0.01 µsec, 0.05 µsec, 0.1 µsec, 0.5 µsec, 1 µsec, 5 µsec, 0.01 msec, 0.05 msec, 0.1 msec, 0.5 msec, 1 msec, 5 msec, 10 msec, 50 msec, 100 msec, 0.5 sec, 1 sec, 5 sec, 10 sec, or 60 sec.

In some embodiments the detector detects the signal at the substrate. In some embodiments the detector will detect the signal in the solution. In some embodiments, the detector will detect signal in both the solution and at the molecular recognition layer.

Where the detector is capable of detecting optical signals, the detector can be, for example a photomultiplier tube (PMT), a CMOS sensor, or a CCD sensor. In some embodiments, the detector comprises a fiber-optic sensor.

In some embodiments, the device comprising the sensor is capable of sensitive fluorescent measurements including synchronous fluorimetry, polarized fluorescent measurements, laser induced fluorescence, fluorescence decay, and time resolved fluorescence.

Optical Layer

The biosensor arrays of the present invention will generally comprise an optical layer. The fully integrated arrays of the present invention comprise an optical layer that at least comprises an optical filter layer. The optical layer resides between the molecular recognition layer and the sensor layer, and transmits the light from the molecular recognition layer to the sensor layer.

An optical layer of the biosensor array can comprises an optical filter layer for transmitting a portion of the spectrum of light from the molecular recognition layer to the sensor layer. The optical filter layer can be a band-pass, stop-band, and/or low-pass optical filter. In a non-limiting example, the optical filter has a bandwidth of about 10 nm to about 20 nm. In this context, the term bandwidth refers to the range of wavelengths that is either passed by a band pass filter, or the range of wavelengths that are stopped by a stop filter. In some embodiments, the optical filter is in the wavelength range of 400 nm to 800 nm.

The choice of the wavelength characteristics of the optical filter layer depends on the characteristics of the fluorescent moieties that are used. In some embodiments, a band-pass filter is used that cuts off light corresponding to excitation, but allows transmission of light corresponding to emission of fluorescence. In some embodiments, the optical filter attenuates fluorescent excitation light by a factor of $10^2$ to $10^7$. In some embodiments, the optical filter attenuates fluorescent excitation light by a factor of $10^3$ to $10^5$.

In some embodiments, the optical filter is a multilayer dielectric filter which covers the transducers.

In some embodiments of the invention with optical layers, the photon flux from the molecular recognition layer is guided to the transducer array, using a plurality of optical waveguides that are of the optical coupling layer. The optical waveguides can operate to essentially map the emitted photon flux from the molecular recognition layer onto the transducer array. The optical coupling layer can comprise a plurality of optical waveguides. Examples of signal coupling elements include fiber optic cables, fiber optic bundles, fiber optic faceplates, and light pipes. Thus, pluralities of transducers and/or spots are optically connected to each other. In further embodiments of this invention, the waveguide is a phaseplate system.

The optical layer can integrate the biochemical part of the microarray with an emission filter and a photo-detector in CMOS where the molecular recognition layer is immobilized on a planar surface of an optical layer. The excitation photon flux tends to be orthogonal to the surface of the microarray, but the emission is in all directions. In order to capture most of the emitted photons, an optical coupling layer comprising a fiber-optic faceplate (FOF) comprising densely packed optical fibers can be positioned on top of the optical filter. The FOF prohibits light scattering and can guide a 2D fluorescence optical pattern along the direction of its fibers. The FOF can be 2 μm to 20 cm thick. In some embodiments, the thickness of the FOF is in the range of about 5 μm to 1 cm. In an embodiment, the thickness of the FOF is 3 mm. The FOF thermally isolates the microarray assay from the CMOS die and photodiodes as well as creating a distance between the aqueous solution and the chip.

Figure 6:
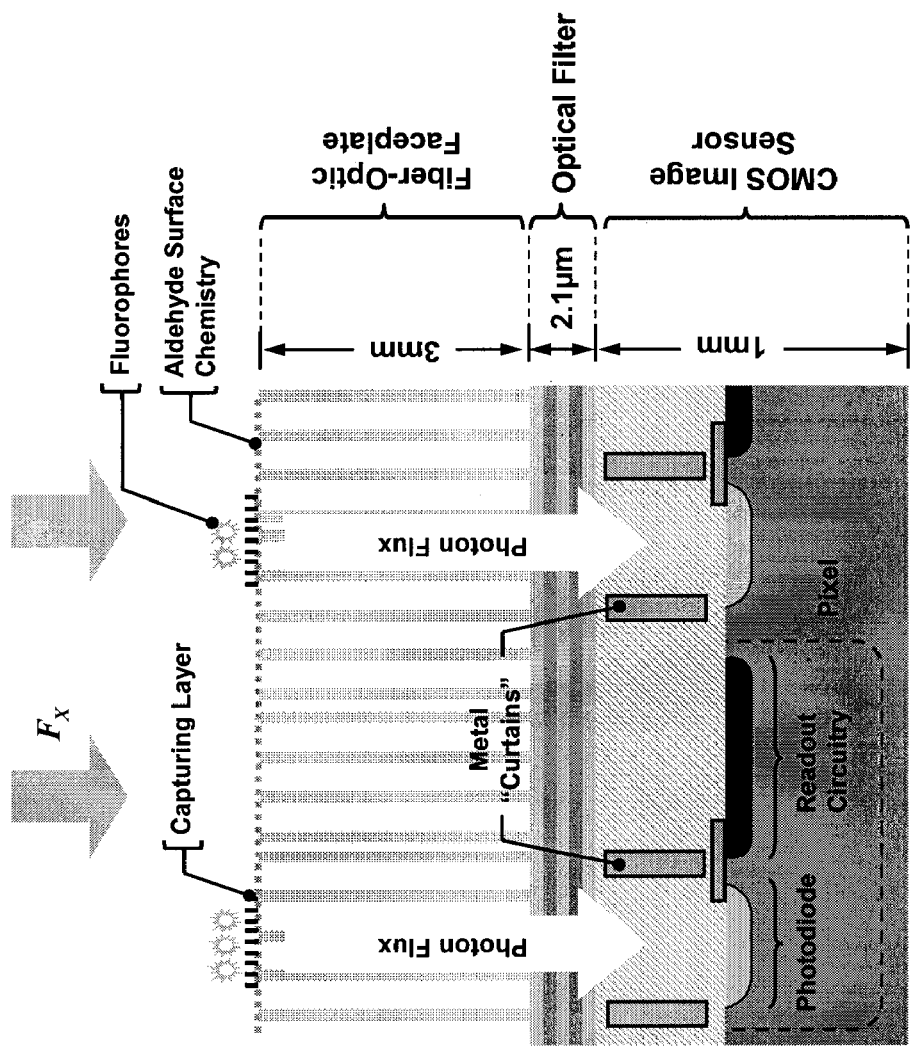
FIG. 6 illustrates an embodiment of the invention comprising a fiber optic faceplate (FOF).

An example device of the invention comprising an FOF is illustrated in FIG. 6. The FOF is located below a capturing (or molecular recognition layer). When the fluorophores are bound to the capture layer, the emitted photon flux can travel through the fiber optics of the FOF in order to send a greater amount of emitted photons to the sensor layer without allowing the excitation photon flux ($F_x$) through to the sensor layer. In this example, the FOF is 3 mm thick and the optical filter layer is 2.1 μm thick. The optical layer can transmit the photon flux from capture layer that has traveled through the FOF to a CMOS image sensor layer. In this example, the CMOS sensor is about 1 mm thick and comprises structures ("metal curtains") for directing the photon flux to a photodiode sensor embedded in the CMOS sensor layer. There are two photodiodes corresponding to the two independently addressable locations on the molecular recognition layer of the example embodiment. Readout circuitry for transmitting the information captured by the photodiodes is also embedded in the CMOS sensor layer.

As an example, the sensor array shown in FIG. 6 can be fabricated using a standard digital 0.35 μm CMOS process in an area of 9 mm². The filter is fabricated using layer-by-layer deposition of dielectric materials to create a long-pass filter with transition wavelength of 560 nm on the FOF. The FOF is the cut to match the sensor array area and placed on top of the CMOS chip. To physically stabilize the FOF on the chip, a non-conductive epoxy is applied on the periphery. The surface functionalization to immobilize the probe is then carried out on the surface of the FOF. In some embodiments, the surface of the FOF can be $SiO_2$ and very similar to the surface of glass slides.

Systems

In an aspect of the invention, a biosensor system is disclosed that comprises an embodiment of a biosensor array of the invention, a light source that directs light to the biosensor array, a fluidic chamber for holding fluid in contact with the biosensor array, a temperature controller for controlling the temperature of the fluid and/or the molecular recognition layer, and an interface that connects to the biosensor array to allow electronic communication to and from the array.

The system typically comprises a light source, for example, for excitation of fluorescence. The light source is generally optically coupled to the substrate, for example with one or more lenses or waveguides. The light source can provide a single wavelength, e.g. a laser, or a band of wavelengths.

The light source that directs light to the biosensor array the light source can be fixed and illuminate some or all of the addressable locations on a molecular recognition layer of the biosensor array.

In an embodiment, the system comprises a plurality of biosensor arrays, wherein at least two of the biosensor arrays are connected to the same computer. In a further embodiment, the system can comprise 2 to 12 biosensor arrays, all of which are connected to the same computer. This system allows for the measurement of binding on multiple arrays simultaneously in one instrument using one computer system.

Control of temperature can be important to allow control of binding reaction rates, e.g. by controlling stringency. The temperature can be controlled by controlling the temperature at any place within the system including controlling the temperature of the fluid or the temperature of the molecular recognition layer. Any temperature control can be used for controlling the temperature including, but not limited to, resistive heaters, Peltier devices, infrared heaters, fluid flow, and gas flow. The temperatures can be the same or different for solution or substrate or different parts of each. In a preferable embodiment, the temperature is consistent within the binding region. In some embodiments, the temperature is controlled to within about 0.01, 0.05, 0.1, 0.5, or 1° C.

In some embodiments, the temperature can be rapidly changed during the binding reaction. The system can be capable of changing the temperature at a rate of temperature change corresponding to a change of 1° C. in less than about 0.01 msec, 0.1 msec, 0.5 msec, 1 msec, 5 msec, 10 msec, 50 msec, 100 msec, 0.5 sec, 1 sec, 10 sec, or 60 sec.

In other embodiments, the temperature is changed slowly, gradually ramping the temperature over the course of the binding reaction.

An example of changing the temperature during the binding reaction involves a change in temperature to change the binding stringency and probability. Many bindings in affinity-based biosensors are a strong function of temperature, thus by changing temperature, the stringency can be altered, and the new capturing process can be observed with a new set of capturing probabilities.

The system can further be capable of measuring temperature at one or multiple locations in the solution or on the biosensor array. The temperature can be measured by any means including, but not limited to, by thermometer, thermocouple, or thermochromic shift.

When temperature is measured, the system can utilize a feedback loop for temperature control wherein the measured temperature is used as an input to the system in order to more accurately control temperature.

A control system of a system of the invention can be a real-time control system for reading the real-time measurements from a biosensor array of the invention.

Figure 7:
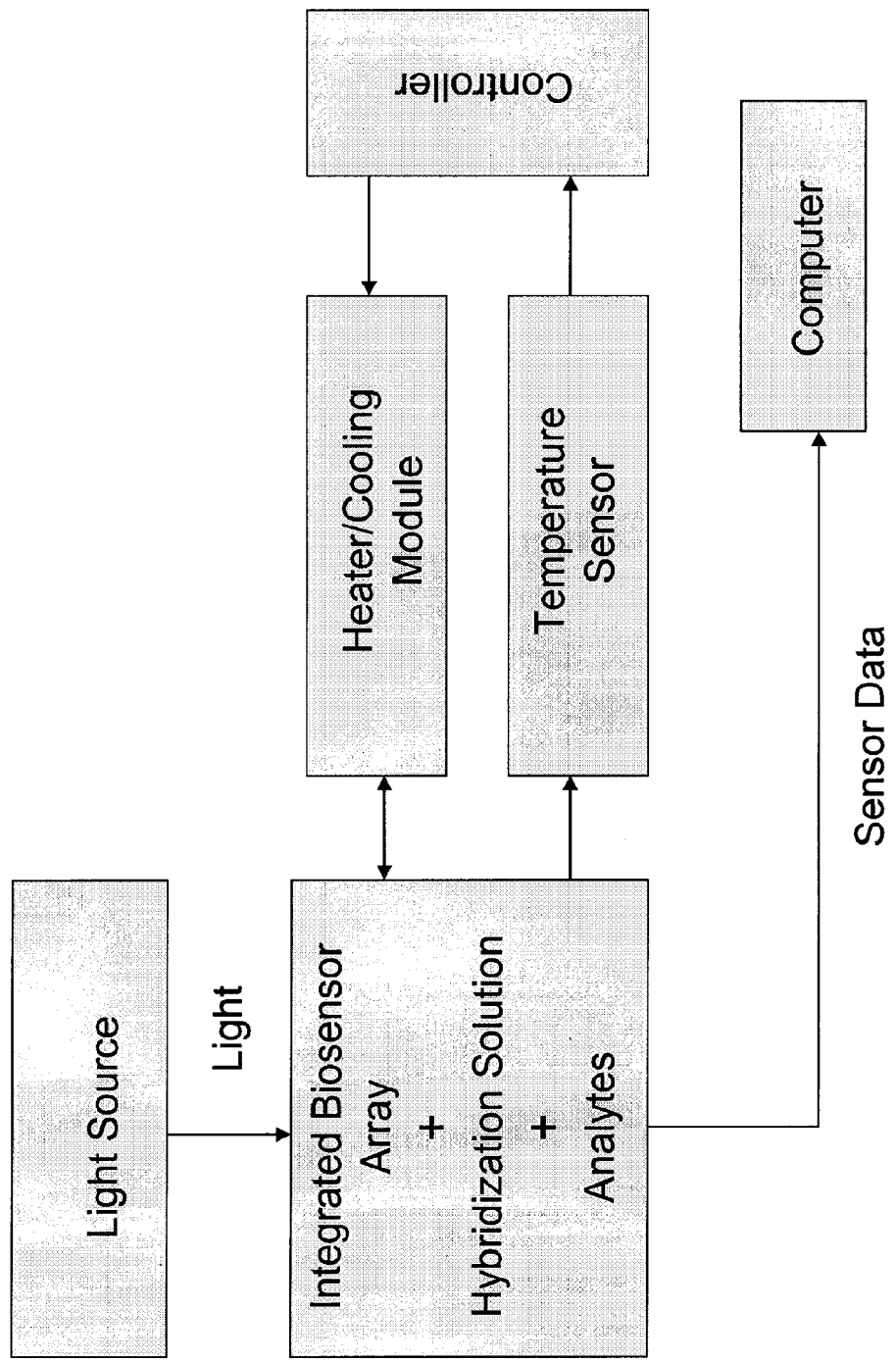
FIG. 7 shows a block diagram of some of the components of systems of the present invention.

FIG. 7 shows a block diagram of some of the components of systems of the present invention. The example system comprises (i) a biosensor array which includes a molecular recognition layer comprising probes and analytes, (ii) a light source for illuminating the molecular recognition layer of the biosensor array, (iii) heating and cooling modules and a temperature sensor, (iv) a temperature controller, and (v) a computer to which sensor data is sent from the biosensor array. In some embodiments, the sensor data will be raw output from the optical sensors. In other embodiments, the sensor data sent to the computer will be further processed by circuits within the optical sensor array.

The system can comprise a computing system for analyzing detected signals. In some embodiments, the system is capable of transferring time point data sets to the computing system wherein each time point data set corresponds to detected signal at a time point, and the computing system is capable of analyzing the time point data sets, in order to determine a property related to the analyte and probe. Thus, a computer system and software that can store and manipulate the data (for instance, images taken at time points) may be components of the system. The data can be analyzed in real-time, as the reaction unfolds, or may be stored for later access.

The information corresponding to a detected signal at each time point can be single values such as signal amplitude, or can be more complex information, for example, where each set of signal information corresponds to an image of a region containing signal intensity values at multiple places within an addressable location.

The property related to analyte and/or probe can be, for example, analyte concentration, binding strength, or competitive binding, and cross-hybridization.

In some embodiments, the computing system uses algorithms for determining concentration and/or cross-hybridization.

The system can also comprise a computer with software for process control and data collection and analysis. The software can be used for characterizing binding between analyte and probe. In one embodiment, the software carries out at least one of the steps of i) accessing stored images taken at different time points, ii) performing image processing to determine the location of the spots and convert the data to a collection of time series (one for each spot) representing the temporal behavior of the signal intensity for each spot, and iii) for each spot on the array determining whether a reaction has happened (this is often done by comparing with control spots on the array). Optionally, the software can perform the steps of iv) determining whether the reaction at each spot involves the binding of a single analyte or multiple analytes (if, for example, cross-hybridization is occurring), v) estimating the reaction rates using statistical system identification methods. Examples of statistical system identification methods include methods such as Prony's method. In the case that step iv) is used, (multiple bindings per spot), the reaction rate of each binding is determined, and vi) using the reaction rates to estimate the unknown quantity of interest (analyte concentration, binding strength, etc.) using, for example, optimal Bayesian methods.

In some embodiments, the system will have software for interfacing with the instrument, for example, allowing the user to display information in real-time and allowing for user to interact with the reaction (i.e., add reagents, change the temperature, change the pH, dilution, etc.).

The system can comprise control circuitry that enables users to activate readout circuits and sensors on the array. The control circuitry can also be used to specify temperature, mixing, fluorescent wavelength, fluorescent excitation power, pressure, and/or humidity. In addition, the control circuitry can be a part of the biosensor array.

In another embodiment, the biosensor system comprises decoder circuitry to select which of a plurality of sensors are to be used. At least part of the decoder circuitry can be part of the biosensor array. The decoder can select which of the plurality of transducers are to be used to analyze the biosensor array probe. The control circuitry enables a user to activate a combination of read-out circuitries and transducers. Further, the system includes a function generator coupled to the control circuitry to generate the experiment control signals. The control signals are connected to systems inside and/or outside the semiconductor substrate. In certain embodiments, the control signal specifies the measurement parameters. These parameters include, but are not limited to, the biosensor array assay temperature, mixing speed, fluorescent excitation signal wavelength, fluorescent excitation power, pressure, and humidity. In further embodiments the control signals are generated by processing the measured signals. The processing can be carried out using a digital signal processor outside the semiconductor substrate and/or an embedded digital signal processing unit inside the semiconductor substrate.

Figure 8:
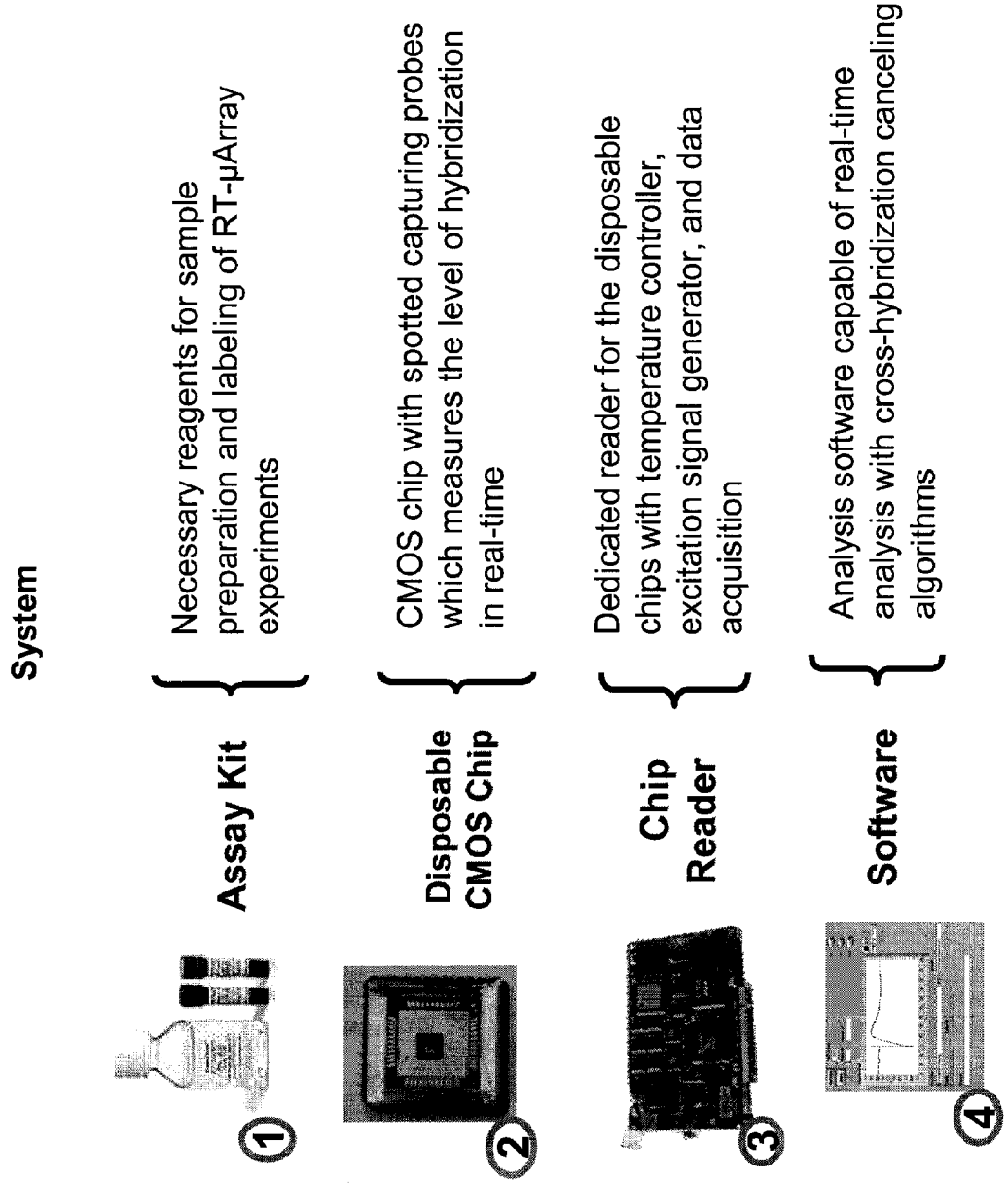
FIG. 8 illustrates an embodiment of a system comprising an assay kit, a disposable sensor chip, a computer chip reader and software for executing a method of the invention.

In an embodiment of the invention illustrated in FIG. 8, a system can comprise an assay kit, a disposable sensor chip, a computer chip reader and software for executing a method of the invention. The assay kit can comprise the necessary reagents for sample preparation and labeling of RT-µArray experiments. The sensor chip can comprise a CMOS chip with spotted capturing probes for measuring the level of hybridization in real-time. The chip reader can be a dedicated reader for the disposable sensor chip and may or may not comprise a temperature controller, excitation signal generator, and data acquisition means.

Methods

The integrated biosensor array devices and systems of the invention can evaluate the abundance of a plurality of target analytes in the sample by real-time detection of target-probe binding events. In certain embodiments, the integrated biosensor arrays are used as RT-µArray detection systems to measure the concentration of the target analytes by analyzing the binding rates and/or the equilibrium concentration and/or the fluctuation of the captured analytes in a single and/or plurality of spots. Applications of integrated biosensor array devices and systems are within the field of Genomics and Proteomics, in particular DNA and Protein microarrays and immunoassays. In some embodiments, the disclosed devices, systems, and methods do not require any washing step and can also measure the probe density variations prior to hybridization (thus allowing for pre-calibration of the experimental results). The RT-µArray systems can also carry out various time averaging schemes to suppress the Poisson noise and fluctuation of target bindings. Since target concentrations can be determined by the reaction rates, it is not necessary for the hybridization process to go to equilibrium, resulting in faster detection times. A goal of the invention is to increase the dynamic range, sensitivity and resolution of microarrays. The invention allows for quality control and may be more amenable to integration and to automation.

Advantages offered by the present invention can also apply to RNA, protein, carbohydrate, or lipid microarrays, to analyze interactions among molecules of the same or of different biochemical nature. In particular, real-time measurements by a platform of the invention, in which interactions are detected as they occur, allows for measuring and comparing rates of analyte binding, affinities, etc. In addition, the RT-µArray can consist of microarrays in which compounds of two different biochemical classes (for example, protein and DNA, or carbohydrate and DNA) are positioned together as a mixture on the same spot of the microarray.

The methods of the present invention can be used for measuring the binding characteristics of multiple probes and analytes in real time. The method is particularly useful for characterizing the binding of probes and analytes which specifically bind to one another. As used herein, a probe "specifically binds" to a specific analyte if it binds to that analyte with greater affinity than it binds to other substances in the sample.

The binding may be a receptor-ligand, enzyme-substrate, antibody-antigen, or a hybridization interaction. The probe/analyte binding pair or analyte/probe binding pair can be nucleic acid to nucleic acid, e.g. DNA/DNA, DNA/RNA, RNA/DNA, RNA/RNA, RNA. The probe/analyte binding pair or analyte/probe binding pair can be a nucleic acid and a polypeptide, e.g. DNA/polypeptide and RNA/polypeptide, such as a sequence specific DNA binding protein. The probe/analyte binding pair or analyte/probe binding pair can be any nucleic acid and a small molecule, e.g. RNA/small molecule, DNA/small molecule. The probe/analyte binding pair or analyte/probe binding pair can be any nucleic acid and synthetic DNA/RNA binding ligands (such as polyamides) capable of sequence-specific DNA or RNA recognition. The probe/analyte binding pair or analyte/probe binding pair can be a protein and a small molecule or a small molecule and a protein, e.g. an enzyme or an antibody and a small molecule.

The probe/analyte binding pair or analyte/probe binding pair can be a carbohydrate and protein or a protein and a carbohydrate, a carbohydrate and a carbohydrate, a carbohydrate and a lipid, or lipid and a carbohydrate, a lipid and a protein, or a protein and a lipid, a lipid and a lipid.

The analyte/probe binding pair can comprise natural binding compounds such as natural enzymes and antibodies, and synthetic binding compounds. The probe/analyte binding pair or analyte/probe binding pair can be synthetic protein binding ligands and proteins or proteins and synthetic binding ligands, synthetic carbohydrate binding ligands and carbohydrates or carbohydrates and synthetic carbohydrate binding ligands, synthetic lipid binding ligands or lipids and lipids and synthetic lipid binding ligands.

In an aspect of the invention, a method is described herein comprising contacting a fluid containing a target analyte with a biosensor array of the invention, illuminating the biosensor, detecting fluorescence on the biosensor, and correlating the detected fluorescence with binding of the target analyte.

In an embodiment, a method of the invention comprises contacting a fluid volume comprising a plurality of different analytes to a molecular recognition layer of the biosensor array that comprises a plurality of different probes at independently addressable locations, wherein the probes are capable of specifically binding to the analytes. The method further comprises measuring signals at multiple time points while the fluid volume is in contact with the molecular recognition layer of a biosensor array, wherein the signals can be correlated with the amount of binding of the analytes with the probes. The biosensor array can comprise an array of optical transducers, wherein at least one optical transducer correlates to an independently addressable location. A change in the signals with time can correlate with the amount of the analytes bound to the probes.

A fluid volume can be introduced and held in a system of the invention by any method that will maintain the fluid in contact with the solid support. In many cases the fluid is held in a chamber. In some embodiments the chamber is open on one face, in other embodiments the chamber will mostly enclose the fluid. In some embodiments, the chamber will have one or more ports for introducing and/or removing material (usually fluids) from the chamber. In some embodiments one side of the chamber comprises the solid substrate on which the probes are attached. In some embodiments the chamber is integral to the solid substrate. In some embodiments, the chamber is a sub-assembly to which the solid substrate with probes can be removably attached. In some embodiments, some or all of the fluid chamber is an integral part of the device that comprises the detector. The chamber can be designed such that the signal that can be correlated with analyte-probe binding can be detected by a detector outside of the chamber. For instance, all or a portion of the chamber can be transparent to light to allow light in or out of the chamber to facilitate excitation and detection of fluorophores.

In some embodiments, the means to perform the assay comprise a compartment wherein the surface of the microarray comprises a floor of the compartment and means to deliver reagents and analytes into the compartment. Any method can be used to seal the microarray to the compartment including using adhesives and gaskets to seal the fluid. Any method can be used to deliver reagents and analytes including using syringes, pipettes, tubing, and capillaries.

In some embodiments, the system comprises an apparatus to add or remove material from the fluid volume. In some embodiments, the system can add or remove a liquid from the fluid volume. In some embodiments, the system is capable of adding or removing material from the fluid volume in order to change the: concentration, pH, stringency, ionic strength, or to add or remove a competitive binding agent. In some embodiments, the system is capable of changing the volume of the fluid volume during the reaction.

One exemplary embodiment of adding material to the fluid volume during the binding reaction comprises the addition of incubation buffer. The incubation buffer is the buffer in which the analytes are residing. By adding the incubation buffer, the concentration of analytes in the system will decrease and therefore the binding probability and kinetic of binding will both decrease. Furthermore, if the reaction has already reached equilibrium, the addition of the buffer will cause the system to move another equilibrium state in time.

Another exemplary embodiment of adding material to the fluid volume during the binding reaction is adding a competing binding species. The competing species can be of the same nature of the analyte but in general they are molecules which have affinity to capturing probes. In DNA microarrays for example, the competing species can be synthesized DNA oligo-nucleotides with partially or completely complementary sequence to the capturing probes. In immunoassays, the competing species are antigens.

In some embodiments, the system comprises elements to apply an electric potential to the fluid volume to electrically change the stringency of the medium. In some embodiments, the system will provide an electrical stimulus to the capturing region using an electrode structure which is placed in proximity of the capturing region. If the analyte is an electroactive species and/or ion, the electrical stimulus can apply an electrostatic force of the analyte. In certain embodiments, this electrostatic force is adjusted to apply force on the bonds between analyte and capturing probe. If the force is applied to detach the molecule, the affinity of the analyte-probe interaction is reduced and thus the stringency of the bond is evaluated. The electrical stimulus is generally a DC and/or time-varying electrical potentials. Their amplitude can be between 1 mV to 10V, but typically between 10 mV to 100 mV. The frequency of time-varying signal can be between 1 Hz to 1000 MHz, in some embodiments, the frequency of the time-varying signal is between 100 Hz to 100 kHz. The use of electric potential to control stringency is described in U.S. Pat. No. 6,048,690.

The method can also further comprise using the signals measured at multiple time points to determine the concentration of an analyte in the fluid volume.

In another aspect of a method of the invention, nucleic acid amplification can be performed on two or more nucleotide sequences with a device of the invention to produce two or more amplicons in a fluid. A similar integrated device for the methods of the invention capable of performing quantitative polymerase chain reactions is described in a co-pending U.S. patent application Ser. No. 11/829,861. The device can comprise a solid surface with a plurality of nucleic acid probes at independently addressable locations, wherein the solid substrate comprises an array of optical transducers, and at least one optical transducer correlates to an independently addressable location. The hybridization of the amplicons to the two or more nucleic acid probes can also be measured while the fluid is in contact with the device to obtain an amplicon hybridization measurement. In a further embodiment, the method further comprises using the amplicon hybridization measurement to determine the concentration of the amplicons in the fluid. In another embodiment the method further comprises using the amplicon hybridization measurement to determine the original amount of nucleotide sequences.

In an embodiment, the method involves the use of probes in which each addressable location emits a signal that is quenchable upon binding of an analyte. For example, the quenchable moiety (e.g., a fluorescent moiety) is attached to the probe on the array or in close physical proximity thereto. The surface of such array will emit signal from each addressable location which can be detected. The analytes in the sample are tagged with a quencher moiety that can quench the signal from the quenchable moiety. When the quencher does not emit a light signal, there is no signal from the fluid to interfere with the signal from the array. This diminishes the noise at the array surface. During the course of a binding reaction between analytes and substrate-bound probes, the signal at each addressable location can be quenched. The signal at each addressable location can be measured in real-time. As the signal at any location changes as a result of binding and quenching, the change is measured. These measurements over time allow determination of the kinetics of the reaction which, in turn, allows determination of the concentration of analytes in the sample.

Alternatively if the analytes are labeled with a light-emitting reporter, such as a fluorescent label, signal at the surface of array resulting from binding of the labeled analyte molecules can be detected by properly focusing the detector at the array surface, thereby minimizing the noise from signal in solution.

In another embodiment, the probes are attached to the surface of an array comprising sensors, such as a CMOS sensor array, which produce electrical signals that change as a result of binding events on the probes. This also affords real-time measurement of a plurality of signals on an array (Hassibi and Lee, IEEE Sensors journal, 6-6, pp. 1380-1388, 2006, and Hassibi, A. "Integrated Microarrays" Ph.D. Thesis Stanford University, 2005).

Accordingly, the methods of this invention allow real-time measurements of a plurality of binding events on an array of probes on a solid support.

Where the probe and analyte are nucleic acids, the present invention provides methods of expression monitoring and generic difference screening. The term expression monitoring is used to refer to the determination of levels of expression of particular, typically preselected, genes. The invention allows for many genes, e.g. 10, 100, 1,000, 10,000, 100,000 or more genes to be analyzed at once. Nucleic acid samples are hybridized to the arrays and the resulting hybridization signal as a function of time provides an indication of the level of expression of each gene of interest. In some embodiments, the array has a high degree of probe redundancy (multiple probes per gene) the expression monitoring methods provide accurate measurement and do not require comparison to a reference nucleic acid.

In another embodiment, this invention provides generic difference screening methods that identify differences in the abundance (concentration) of particular nucleic acids in two or more nucleic acid samples. The generic difference screening methods involve hybridizing two or more nucleic acid samples to the same oligonucleotide array, or to different oligonucleotide arrays having the same oligonucleotide probe composition, and optionally the same oligonucleotide spatial distribution. The resulting hybridizations are then compared allowing determination which nucleic acids differ in abundance (concentration) between the two or more samples.

Where the concentrations of the nucleic acids comprising the samples reflects transcription levels genes in a sample from which the nucleic acids are derived, the generic difference screening methods permit identification of differences in transcription (and by implication in expression) of the nucleic acids comprising the two or more samples. The differentially (e.g., over- or under-) expressed nucleic acids thus identified can be used (e.g., as probes) to determine and/or isolate those genes whose expression levels differs between the two or more samples.

The expression monitoring and difference screening methods of this invention may be used in a wide variety of circumstances including detection of disease, identification of differential gene expression between two samples (e.g., a pathological as compared to a healthy sample), screening for compositions that upregulate or down-regulate the expression of particular genes, and so forth.

Analyte and Probe

The terms "probe" and "analyte" as used herein refer to molecular species that bind to one another in solution. A single probe or a single analyte is generally one chemical species. That is, a single analyte or probe may comprise many individual molecules. In some cases, a probe or analyte may be a set of molecules that are substantially identical. In some cases a probe or analyte can be a group of molecules all of which have a substantially identical binding region. A "probe" and/or "analyte" can be any pair of molecules that bind to one another, including for example a receptor/ligand pair, or a hybridizing pair of nucleic acids. In probes of the present invention are bound to a solid surface. The analyte is in solution, and can also be referred to as the target or the target analyte. Thus, while the probe and analyte can interchangeably be the different members of any binding pair, in some cases it is more advantageous for one or the other to be the probe or the analyte, for instance where the molecule is more easily coupled to the surface, it can be advantageous for that molecule to be the probe, or where a molecule is more soluble in the solution of interest, it can be advantageous for that molecule to be the analyte.

The probes or analytes can be any type of chemical species. The probes or analytes are generally biomolecules such as nucleic acids, proteins, carbohydrates, lipids, or small molecules. The probe and analyte which bind to one another can each be the same or different types of species. The analyte or probe may be bound to another type of molecule and may comprise different molecules. For example, an analyte could be a protein carbohydrate complex, or a nucleic acid connected to protein. A probe-analyte pair can also be a receptor-ligand pair. Where the chemical species is large or made of multiple molecular components, the probe or analyte may be the portion of the molecule that is capable of binding, or may be the molecule as a whole. Examples of analytes that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, antibodies, and hybridizing nucleic acids.

The term "probe" is used herein to refer to the member of the binding species that is attached to a surface. For instance, the probe consists of biological materials deposited so as to create spotted arrays; and materials synthesized, deposited, or positioned to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media. The construction of various probe arrays of the invention are described in more detail below.

In some embodiments, the probe and/or the analyte comprises a polynucleotide. The terms "polynucleotide," "oligonucleotide," "nucleic acid" and "nucleic acid molecule" as used herein include a polymeric form of nucleotides of any length, either ribonucleotides (RNA) or deoxyribonucleotides (DNA). This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotide backbones. A nucleic acid of the present invention will generally contain phosphodiester bonds, although in some cases, as outlined below, nucleic acid analogs are included that may have alternate backbones, comprising, for example, phosphoramide (U.S. Pat. No. 5,644,048), phosphorodithioate (Briu et al., J. Am. Chem. Soc. 11 1:2321 (1989), O-methylphosphoroamidite linkages and peptide nucleic acid backbones and linkages (see Carlsson et al., Nature 380:207 (1996)). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863, including those described in U.S. Pat. Nos. 5,235,033 and 5,034,506. Nucleic acids containing one or more carbocyclic sugars are also included within the definition of nucleic acids. These modifications of the ribose-phosphate backbone may be done to facilitate the addition of labels, or to increase the stability and half-life of such molecules in physiological environments.

In some embodiments of the invention, oligonucleotides are used. An "oligonucleotide" as used herein is a single-stranded nucleic acid ranging in length from 2 to about 1000 nucleotides, more typically from 2 to about 500 nucleotides in length. In some embodiments, it is about 10 to about 100 nucleotides, and in some embodiments, about 20 to about 50 nucleotides.

In some embodiments of the invention, for example, expression analysis, the invention is directed toward measuring the nucleic acid concentration in a sample. In some cases the nucleic acid concentration, or differences in nucleic acid concentration between different samples, reflects transcription levels or differences in transcription levels of a gene or genes. In these cases it can be desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In the simplest embodiment, such a nucleic acid sample is the total mRNA or a total cDNA isolated and/or otherwise derived from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

In some embodiments, the probe and or the analyte may comprise a polypeptide. As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. The "peptide" refers to polypeptides of no more than about 50 amino acids, while term "protein" refers to longer polypeptides, typically with three-dimensional structures. Non-natural polypeptides containing one or more analogs of an amino acid (including, for example, unnatural amino acids, etc.), can also be useful in the invention, as can polypeptides with substituted linkages, as well as other modifications known in the art, both naturally occurring and non-naturally occurring. Polypeptides and proteins can have specific binding properties. For instance, an enzyme can have a region that binds specifically with a substrate, and/or has regions that bind to other proteins, such as the binding of enzyme subunits. Antibodies, which can have very specific binding properties are also polypeptides.

In some embodiments the probe and/or analyte can comprise a carbohydrate such as a polysaccharide. The term polysaccharide, as used herein, refers to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Monosaccharides include, but are not limited to, ribose, 2-deoxy-ribose, glucose, mannose, xylose, galactose, fucose, fructose, etc. Disaccharides contain two monosaccharide units joined by a glycosidic linkage. Disaccharides include, for example, sucrose, lactose, maltose, cellobiose, and the like. Oligosaccharides typically contain from 2 to 10 monosaccharide units joined in glycosidic linkage. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc. A saccharide may also reside as a component part of a larger molecule, for example, as the saccharide moiety of a nucleoside, a nucleotide, a polynucleotide, a DNA, an RNA, etc.

In some embodiments, the analyte and/or probe is a small molecule. Generally the small molecule will be an organic molecule, for example, biotin or digoxigenin, but in some cases, the analyte can be inorganic, for example an inorganic ion such as lithium, sodium, ferric, ferrous, etc. The small molecule can also be an organometallic compound, having both inorganic and organic components.

Optical Detection of Signals

For the methods of the present invention, a signal is detected that can be correlated with the binding of analytes to the plurality of probes. The type of signals appropriate for the invention is any signal that can be amount of analyte bound to the plurality of probes.

Examples of optical signals useful in the present invention are signals from fluorescence, luminescence, and absorption. As used herein, the terms "electromagnetic" or "electromagnetic wave" and "light" are used interchangeably. Electromagnetic waves of any frequency and wavelength that can be correlated to the amount of analyte bound to probe on the surface can be used in the present invention including gamma rays, x-rays, ultraviolet radiation, visible radiation, infrared radiation, and microwaves. While some embodiments are described with reference to visible (optical) light, the descriptions are not meant to limit the embodiments to those particular electromagnetic frequencies.

For the methods of the present invention it is desired that the signal changes upon the binding of the analyte to the probe in a manner that correlates with the amount of analyte bound. In some cases, the change in signal will be a change in intensity of the signal. In some embodiments, the signal intensity will increase as more analyte is bound to probe. In some embodiments, the signal intensity will decrease as more analyte is bound to probe. In some embodiments, the change in signal is not a change in intensity, but can be any other change in the signal that can be correlated with analyte binding to probe. For example, the change in signal upon binding of the probe can be a change in the frequency of the signal. In some embodiments, the signal frequency will increase as more analyte is bound to probe. In some embodiments, the signal frequency will decrease as more analyte is bound to the probe.

The signal that is measured is generally the signal in the region of the solid surface. In some embodiments, signal from moieties attached to the surface is used as the signal that can be correlated with the amount of analyte bound to the probe. In some embodiments signal from the solution is used as the signal that can be correlated with the amount of analyte bound to the probe.

In some embodiments of the methods of the present invention, labels are attached to the analytes and/or the probes. Any label can be used on the analyte or probe which can be useful in the correlation of signal with the amount of analyte bound to the probe. It would be understood by those of skill in the art that the type of label with is used on the analyte and/or probe will depend on the type of signal which is being used, for example, as described above, a dense label for a mechanical signal, or a redox active label for a voltammetric measurement.

In some embodiments, the signal that can be correlated to the amount of analyte bound to probe is due to the buildup of label at the surface as more analyte is bound to the probes on the surface. For example, where the analyte has a fluorescent label, as more analyte binds, the intensity of the fluorescent signal can increase in a manner that can be correlated with the amount of analyte bound to probe on the surface. In some embodiments, the signal that can be correlated to the amount of analyte bound to probe is due to the release of label from the surface. For example, where the probe has a fluorescent label and the label is released into solution upon the binding of the analyte to the probe, the fluorescent intensity at the surface will decrease as more analyte is bound and more fluorescent label is released.

In some embodiments, the signal that can be correlated to the amount of analyte bound to probe is due to a change in the signal from label on the surface upon binding of the analyte to the probe. For example, where a fluorescent label is on the surface, and the analyte is labeled with a compound capable of changing the fluorescent signal of the surface fluorescent label upon binding of the analyte with the probe, the change in signal can be correlated with the amount of analyte bound to probe. In some embodiments, the analyte is labeled with a quencher, and the decrease in intensity from the surface fluorescent label due to quenching is correlated to the increased amount of analyte bound to probe. In some embodiments, the analyte is labeled with a fluorescent compound which can undergo energy transfer with the fluorescent label on the surface such that the increase in fluorescence from the analyte fluorescent label and/or the decrease in fluorescence from the surface fluorescent label can be correlated with the amount of analyte bound to probe. In some embodiments the surface fluorescent label is bound directly, e.g. covalently to the probe. In some embodiments, the surface fluorescent label is bound to the surface, is not bound to the probe, but is in sufficient proximity that the binding of the analyte to the probe produces a change in signal from the surface fluorescent label that can be correlated with the amount of analyte bound to probe.

In some embodiments, the analyte is unlabeled, and the binding characteristics and or concentration of the analyte is determined by competitive binding with another labeled species, which competes with the analyte for biding to a probe. For example, where we have a solution with an analyte, A, whose concentration we want to determine, and we have a competitive binding species, B, whose binding characteristics with probe and whose concentration are known, then using the present invention, we can use, for example, an array of probes on a surface to determine the concentration of A by determining the amount of competitive binding of B to a probe. For example, the probe is attached to a surface that is fluorescently labeled, and B is labeled with a quencher such that the level of quenching of the surface fluorescence can be correlated with the amount of B bound to the probe. The rate of binding of B to the probe is measured in real time, and the concentration of A is determined by knowing the characteristics of A as a competitive binder. In some embodiments, the amount of the competitive binding species does not need to be known beforehand. For instance, the kinetics of binding of be can be measured in the fluid volume, then the conditions can be changed, (e.g. increasing the stringency) such that B is released from the probe, then the analyte A is added, and the binding of B under competition with A is measured. This example illustrates an advantage of the being able to change the conditions of the medium during one experiment. In some cases, A and B can be the same species, where B is labeled, and the amount of B is known, and the amount of A can be determined by the kinetics of the binding of B. In some cases, A and B are not the same species, but compete for binding with a probe. This competitive binding real-time assay can be done with all types of molecular species described herein including nucleic acids, antibodies, enzymes, binding proteins, carbohydrates and lipids.

Some embodiments of the invention involve measuring light absorption, for example by dyes. Dyes can absorb light within a given wavelength range allowing for the measurement of concentration of molecules that carry that dye. In the present invention, dyes can be used as labels, either on the analyte or on the probe. The amount of dye can be correlated with the amount of analyte bound to the surface in order to determine binding kinetics. Dyes can be, for example, small organic or organometallic compounds that can be, for example, covalently bound to the analyte to label the analyte. Dyes which absorb in the ultraviolet, visible, infrared, and which absorb outside these ranges can be used in the present invention. Methods such as attenuated total reflectance (ATR), for example for infrared, can be used to increase the sensitivity of the surface measurement.

Some embodiments of the invention involve measuring light generated by luminescence. Luminescence broadly includes chemiluminescence, bioluminescence, phosphorescence, and fluorescence. In some embodiments, chemiluminescence, wherein photons of light are created by a chemical reaction such as oxidation, can be used. Chemiluminescent species useful in the invention include, without limitation, luminol, cyalume, TMAE (tetrakis(dimethylamino)ethylene), oxalyl chloride, pyrogallol (1,2,3-trihydroxibenzene), lucigenin. In some embodiments, bioluminescence is used. Where the luminescence is bioluminescence, creation of the excited state derives from an enzyme catalyzed reaction. Bioluminescence derives from the capacity of living organisms to emit visible light through a variety of chemiluminescent reaction systems. Bioluminescence generally include three major components: a luciferin, a luciferase and molecular oxygen. However other components may also be required in some reactions, including cations ($Ca^{++}$ and $Mg^{++}$) and cofactors (ATP, NAD(P)H). Luciferases are enzymes that catalyze the oxidation of a substrate, luciferin, and produce an unstable intermediate. Light is emitted when the unstable intermediate decays to its ground state, generating oxyluciferin. Any of the different unrelated types of luciferin can be used herein including those from phyla which use a luciferin, known as coelenterazine, which contains a ring formed by three amino acids (2 tyrosines, and a phenylalanine). Photoproteins from animals such as jellyfish can be used where the "photoprotein" of the luciferin/luciferase system emits light upon calcium binding. Other bioluminescent systems as described in U.S. Patent Application Publication No. 2007/0065818, and including bioluminescence resonance energy transfer (BRET) as described in U.S. Patent Application Publication No. 2007/0077609 can be used in the present invention.

Fluorescent Systems

A useful embodiment of the present invention involves the use of fluorescence. As used herein, fluorescence refers to the process wherein a molecule relaxes to its ground state from an electronically excited state by emission of a photon. As used herein, the term fluorescence also encompasses phosphorescence. For fluorescence, a molecule is promoted to an electronically excited state by generally by the absorption of ultraviolet, visible, or near infrared radiation. The excited molecule then decays back to the ground state, or to a lower-lying excited electronic state, by emission of light. An advantage of fluorescence for the methods of the invention is its high sensitivity. Fluorimetry may achieve limits of detection several orders of magnitude lower than for absorption. Limits of detection of $10^{-10}$ M or lower are possible for intensely fluorescent molecules; in favorable cases under stringently controlled conditions, the ultimate limit of detection (a single molecule) may be reached.

A wide variety of fluorescent molecules can be utilized in the present invention including small molecules, fluorescent proteins and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

Some embodiments of the present invention include the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750. Some embodiments of the present invention include the Cy Dye fluorophore series (GE Healthcare), also covering a wide spectrum such as Cy3, Cy3B, Cy3.5, Cy5, Cy5.5, Cy7. Some embodiments of the present invention include the Oyster dye fluorophores (Denovo Biolabels) such as Oyster-500, -550, -556, 645, 650, 656. Some embodiments of the present invention include the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL. Some embodiments of the present invention include the ATTO fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740. Some embodiments of the present invention include CAL Fluor and Quasar dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670. Some embodiments of the present invention include quantum dots such as the EviTags (Evident Technologies) or quantum dots of the Qdot series (Invitrogen) such as the Qdot 525, Qdot565, Qdot585, Qdot605, Qdot655, Qdot705, Qdot 800. Some embodiments of the present invention include fluorescein, rhodamine, and/or phycoerythrin.

FRET and Quenching

In some embodiments of the invention, fluorescence resonance energy transfer is used to produce a signal that can be correlated with the binding of the analyte to the probe. FRET arises from the properties of certain fluorophores. In FRET, energy is passed non-radiatively over a distance of about 1-10 nanometers between a donor molecule, which is a fluorophore, and an acceptor molecule. The donor absorbs a photon and transfers this energy non-radiatively to the acceptor (Forster, 1949, Z. Naturforsch. A4: 321-327; Clegg, 1992, Methods Enzymol. 211: 353-388). When two fluorophores whose excitation and emission spectra overlap are in close proximity, excitation of one fluorophore will cause it to emit light at wavelengths that are absorbed by and that stimulate the second fluorophore, causing it in turn to fluoresce. The excited-state energy of the first (donor) fluorophore is transferred by a resonance induced dipole-dipole interaction to the neighboring second (acceptor) fluorophore. As a result, the excited state lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (up to 7 to 10 nanometers. The efficiency of energy transfer can falls off rapidly with the distance between the donor and acceptor molecules.

Molecules that can be used in FRET include the fluorophores described above, and includes fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In some embodiments of the methods of the present invention, the acceptor of the FRET pair is used to quench the fluorescence of the donor. In some cases, the acceptor has little to no fluorescence. The FRET acceptors that are useful for quenching are referred to as quenchers. Quenchers useful in the methods of the present invention include, without limitation, Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare), which can be used, for example, in conjunction with donor fluors such as Cy3B, Cy3, or Cy5; DY-Quenchers (Dyomics), such as DYQ-660 and DYQ-661; and ATTO fluorescent quenchers (ATTO-TEC GmbH), such as ATTO 540Q, 580Q, 612Q.

In some embodiments of the methods of the invention, both the analytes and the probes have labels that are members of a FRET pair, and the labels are attached such that when an analyte binds to a probe, FRET will occur between the labels, resulting in a change in signal that can be correlated with the binding of analyte to probe in real-time. The change in signal can be the decrease in the intensity of the donor and/or the increase in the intensity of the acceptor. The FRET pair can be chosen such that emission wavelength of the donor fluorophore is far enough from the emission wavelength of the acceptor fluorophore, that the signals can be independently measured. This allows the measurement of both the decrease in signal from the donor and the increase in signal from the acceptor at the same time, which can result in improvements in the quality of the measurement of binding. In some cases, the probe will have a label that is the donor of the donor-acceptor pair. In some cases, the analyte will have a label that is the donor of the donor acceptor pair.

In some embodiments of the methods of the invention, the analyte will have a fluorescent label that is a member of a FRET pair, and the other member of the FRET pair will be attached to the surface, wherein the member of the FRET pair attached to the surface is not covalently linked to the probe. In some cases, the analyte will have a label that is the donor of the donor-acceptor pair. In some cases, the analyte will have a label that is the acceptor of the donor acceptor pair. In some embodiments, the member of the FRET pair that is attached to the surface is attached to an oligonucleotide which is attached to the surface (a surface-bound label). The oligonucleotide that is labeled with the FRET pair can be a nucleotide sequence that does not have a sequence anticipated to specifically bind to an analyte. The use of a surface-bound label allows for the labeling of multiple areas of an array without having to label each specific binding probe. This can simplify the production of the array and reduce costs. We have found that even though the surface-bound FRET pairs are not covalently bound to the probe, they can be sensitive to the binding of the analyte labeled with the other member of the FRET pair in a manner that allows the change in signal to be correlated with the amount of analyte bound to probe.

In some embodiments of the methods of the present invention, the analyte is labeled with a quencher, and the probe is labeled with a donor fluorophore. The analyte is labeled with the quencher such that when analyte binds with the probe, the fluorescence from the fluorescent label on the probe is quenched. Thus, the signal, measured in real-time, can be correlated with the amount of binding of the analyte and the probe, allowing for the measurement of the kinetics of the binding. In some embodiments of the methods of the present invention, the analyte is labeled with a quencher, and the probe is labeled with a donor fluorophore, that is not covalently attached to it. The quencher is labeled such that when analyte binds with the probe, the fluorescence from the fluorescent label on the probe is quenched. Thus, the signal, measured in real-time, can be correlated with the amount of binding of the analyte and the probe, allowing for the measurement of the kinetics of the binding.

In some embodiments of the methods of the present invention, the analyte is labeled with a quencher, and the surface is labeled with a donor fluorophore wherein the donor fluorophore is not covalently linked to the probe (e.g. with a surface bound fluorescent label). The quencher is labeled such that when analyte binds with the probe, the fluorescence from the fluorescent label on the surface is quenched. Thus, the signal, measured in real-time, can be correlated with the amount of binding of the analyte and the probe, allowing for the measurement of the kinetics of the binding.

Where the probe is labeled with a fluorophore, one aspect of the invention is the use of an image of the fluorescently labeled probe on the surface obtained before binding has occurred in order to effectively establish a baseline signal for the state where no binding of analyte to probe has occurred. In conventional arrays, in which unlabeled probe is treated with labeled analyte, and the signal is measured after hybridization and washing, it can be difficult to know exactly how much probe is actually on the array in the region of interest. Thus, differences in array manufacture can affect the quality of the data. In the present invention, where the probe is labeled with fluorophore, the image of the labeled probe on the surface provides a measurement of the amount of probe actually on the surface, increasing the quality and reliability of the binding measurement.

Nucleic Acid Systems

One particularly useful aspect of the present invention involves specific hybridization between an analyte and a probe, where both comprise nucleic acids.

As used herein an "oligonucleotide probe" is an oligonucleotide capable of binding to a target nucleic acid of complementary sequence through one or more types of chemical bonds, usually through complementary base pairing, usually through hydrogen bond formation. The oligonucleotide probe may include natural (i.e. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages. The oligonucleotide probes can also comprise locked nucleic acids (LNA), LNA, often referred to as inaccessible RNA, is a modified RNA nucleotide. The ribose moiety of the LNA nucleotide is modified with an extra bridge connecting 2' and 4' carbons. The bridge "locks" the ribose in 3'-endo structural conformation, which is often found in A-form of DNA or RNA. LNA nucleotides can be mixed with DNA or RNA bases in the oligonucleotide. Such oligomers are commercially available. The locked ribose conformation can enhance base stacking and backbone pre-organization, and can increase the thermal stability (melting temperature) of oligonucleotides.

The term "nucleic acid analyte" or "target nucleic acid" or "target" refers to a nucleic acid (often derived from a biological sample and hence referred to also as a sample nucleic acid), to which the oligonucleotide probe specifically hybridizes. It is recognized that the target nucleic acids can be derived from essentially any source of nucleic acids (e.g., including, but not limited to chemical syntheses, amplification reactions, forensic samples, etc.). It is either the presence or absence of one or more target nucleic acids that is to be detected, or the amount of one or more target nucleic acids that is to be quantified. The target nucleic acid(s) that are detected preferentially have nucleotide sequences that are complementary to the nucleic acid sequences of the corresponding probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. The difference in usage will be apparent from context.

In the present invention, the specific hybridization of an oligonucleotide probe to the target nucleic acid can be measured in real-time. An oligonucleotide probe will generally hybridize, bind, or duplex, with a particular nucleotide sequence under stringent conditions even when that sequence is present in a complex mixture. The term "stringent conditions" refers to conditions under which a probe will hybridize preferentially to its target subsequence, and to a lesser extent to, or not at all to, other sequences.

For nucleic acid systems, the oligonucleotide probes of the present invention are designed to be complementary to a nucleic acid target sequence, such that hybridization of the target sequence and the probes of the present invention occurs. This complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, an oligonucleotide probe that is not substantially complementary to a nucleic acid analyte will not hybridize to it under normal reaction conditions.

The methods of the present invention thus can be used, for example, to determine the sequence identity of a nucleic acid analyte in solution by measuring the binding of the analyte with known probes. The sequence identity can be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity.

The methods of the current invention when applied to nucleic acids, can be used for a variety of applications including, but not limited to, (1) mRNA or gene expression profiling, involving the monitoring of expression levels for example, for thousands of genes simultaneously. These results are relevant to many areas of biology and medicine, such as studying treatments, diseases, and developmental stages. For example, microarrays can be used to identify disease genes by comparing gene expression in diseased and normal cells; (2) comparative genomic hybridization (Array CGH), involving the assessment of large genomic rearrangements; (3) SNP detection arrays for identifying for Single Nucleotide Polymorphisms (SNP's) in the genome of populations; and chromatin immunoprecipitation (chIP) studies, which involve determining protein binding site occupancy throughout the genome, employing ChIP-on-chip technology.

The present invention can be very sensitive to differences in binding between nucleic acid species, in some cases, allowing for the discrimination down to a single base pair mismatch. And because the present invention allows the simultaneous measurement of multiple binding events, it is possible to analyze several species simultaneously, where each is intentionally mismatched to different degrees. In order to do this, a "mismatch control" or "mismatch probe" which are probes whose sequence is deliberately selected not to be perfectly complementary to a particular target sequence can be used, for example in expression arrays. For each mismatch (MM) control in an array there, for example, exists a corresponding perfect match (PM) probe that is perfectly complementary to the same particular target sequence. In "generic" (e.g., random, arbitrary, haphazard, etc.) arrays, since the target nucleic acid(s) are unknown, perfect match and mismatch probes cannot be a priori determined, designed, or selected. In this instance, the probes can be provided as pairs where each pair of probes differs in one or more pre-selected nucleotides. Thus, while it is not known a priori which of the probes in the pair is the perfect match, it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3, 4, 5, or more) of probes that differ from each other in particular preselected nucleotides. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

It will be understood by one of skill in the art that control of the characteristics of the solution such as the stringency are important in using the present invention to measure the binding characteristics of a analyte-probe pair, or the concentration of a nucleic acid analyte (target nucleic acid). A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). In some embodiments, highly stringent conditions are used. In other embodiments, less stringent hybridization condition; for example, moderate or low stringency conditions may be used, as known in the art; see Maniatis and Ausubel, supra, and Tijssen, supra. The hybridization conditions may also vary when a non-ionic backbone, i.e. PNA is used, as is known in the art.

Stringent conditions are sequence-dependent and will be different in different circumstances. Longer sequences tend to hybridize specifically at higher temperatures. Generally, stringent conditions can be selected to be about 5.degree. C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target analyte sequences are generally present in excess, at $T_m$, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

In some embodiments, the probe and or the analyte may comprise an antibody. As used herein, the term "antibody" refers to an immunoglobulin molecule or a fragment of an immunoglobulin molecule having the ability to specifically bind to a particular molecule, referred to as an antigen. The antibody may be an anti-receptor antibody specific for the receptor used in the assay. Thus, the antibody may be capable of specifically binding the receptor as the antigen. Antibodies and methods for their manufacture are well known in the art of immunology. The antibody may be produced, for example, by hybridoma cell lines, by immunization to elicit a polyclonal antibody response, or by recombinant host cells that have been transformed with a recombinant DNA expression vector that encodes the antibody. Antibodies include but are not limited to immunoglobulin molecules of any isotype (IgA, IgG, IgE, IgD, IgM), and active fragments including Fab, Fab', F(ab')$_2$, Facb, Fv, ScFv, Fd, $V_H$ and $V_L$. Antibodies include but are not limited to single chain antibodies, chimeric antibodies, mutants, fusion proteins, humanized antibodies and any other modified configuration of an immunoglobulin molecule that comprises an antigen recognition site of the required specificity.

The preparation of antibodies including antibody fragments and other modified forms is described, for example, in "Immunochemistry in Practice," Johnstone and Thorpe, Eds., Blackwell Science, Cambridge, Mass., 1996; "Antibody Engineering," 2nd edition, C. Borrebaeck, Ed., Oxford University Press, New York, 1995; "Immunoassay", E. P. Diamandis and T. K. Christopoulos, Eds., Academic Press, Inc., San Diego, 1996; "Handbook of Experimental Immunology," Herzenberg et al., Eds, Blackwell Science, Cambridge, Mass., 1996; and "Current Protocols in Molecular Biology" F. M. Ausubel et al., Eds., Greene Pub. Associates and Wiley Interscience, 1987, the disclosures of which are incorporated herein. A wide variety of antibodies also are available commercially.

In some embodiments, the probe and or the analyte may comprise two proteins. Protein-protein interactions can enable two or more proteins to associate. A large number of non-covalent bonds can form between the proteins when two protein surfaces are precisely matched, and these bonds account for the specificity of recognition. Protein-protein interactions are involved, for example, in the assembly of enzyme subunits; of multiprotein enzymatic complexes, or of molecular machines; in enzyme-substrate reactions; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein-protein interactions. For example, some oncogenes encode protein kinases whose enzymatic activity on cellular target proteins leads to the cancerous state. Another example of a protein-protein interaction occurs when a virus infects a cell by recognizing a polypeptide receptor on the surface, and this interaction has been used to design antiviral agents. In some cases, protein-protein interactions can be dependent on protein modifications. For example, histone proteins can be modified at different positions with different chemical tags (e.g. phosphorylation, or methylation), and the modifications themselves be required or involved in the recognition by other proteins (e.g chromatin remodeling and associated proteins).

Example 1

Figure 9:
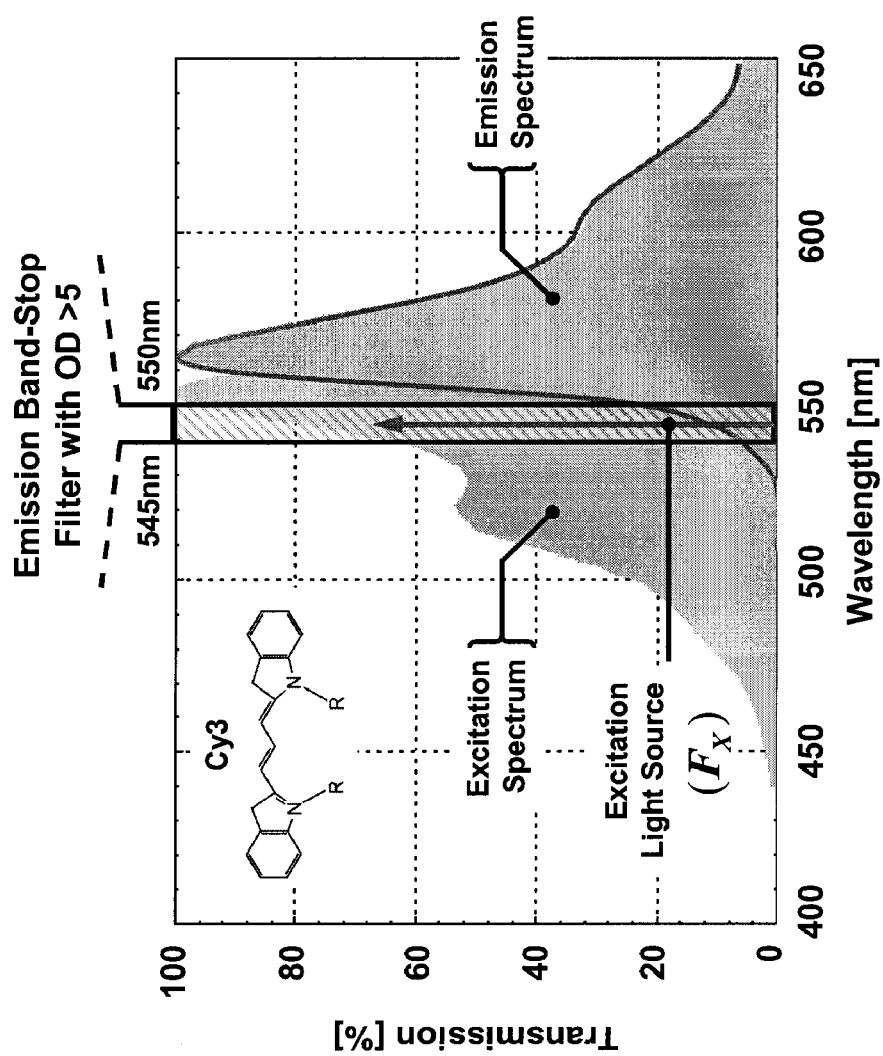
FIG. 9 illustrates the absorption and emission spectra of Cy3 molecule.

This example illustrates how an optical filter layer in the form of a band-pass filter on the surface of the CMOS chip enhances optical performance of the integrated biosensor array. A challenge of designing any fluorescent-based detector is the proper optical excitation and detection of fluorescent labels. FIG. 9 illustrates the absorption and emission spectra of Cy3 molecule which is an example fluorophore of a system. The absorbed photon density for Cy3, denoted by A, exposed to the incident photon flux, $F_X$, obeys the Beer-Lambert law. For a thin layer of diluted absorbing media with Cy3 as in microarray applications we have $$A = F_X[1 - e^{-a_0(\lambda)N}] \approx F_X a_0(\lambda)N, \quad (1)$$

where $a_0(\lambda)$ and N are the extinction coefficient in wavelength $\lambda$ and surface concentration of Cy3 respectively. Considering $Q_Y$, the fluorescence quantum yield of Cy3, we can calculate $I_E$, the total emitted photons per surface area by $$I_E = Q_Y A \approx Q_Y F_X a_0(\lambda)N \quad (2)$$

As evident in FIG. 9, the photon emission is, to first order, proportional to N which is parameter of interest in microarrays. The major impediment for measuring $I_E$ and therefore N, is the presence of $F_X$ during detection. Although $F_X$ has a different wavelength from $I_E$, is very typical for $F_X$ to be to 4-5 orders of magnitude larger than $I_E$ in microarray applications. To block $F_X$ in our system, a multi-layer dielectric Fabry-Perot optical band-pass filter has been fabricated on the surface of a CMOS chip. This emission filter can block $F_X$ by 100 dB in the Cy3 excitation band of 545-550 nm, while only loosing 25% of the signal in the pass-band.

Example 2

This example describes the construction of a fully integrated biosensor array of the present invention. To design the CMOS photo-detector a Nwell/Psub photodiode array is used in the 0.35 µm CMOS process. Each diode is 50 µm×50 µm and the array pitch is 250 µm. This dimension is compatible with commercial microarray specifications and also minimizes the optical cross-talk between photodiodes while providing sufficient space to integrate in-pixel a photocurrent detector and an analog to digital converter (ADC).

Figure 10:
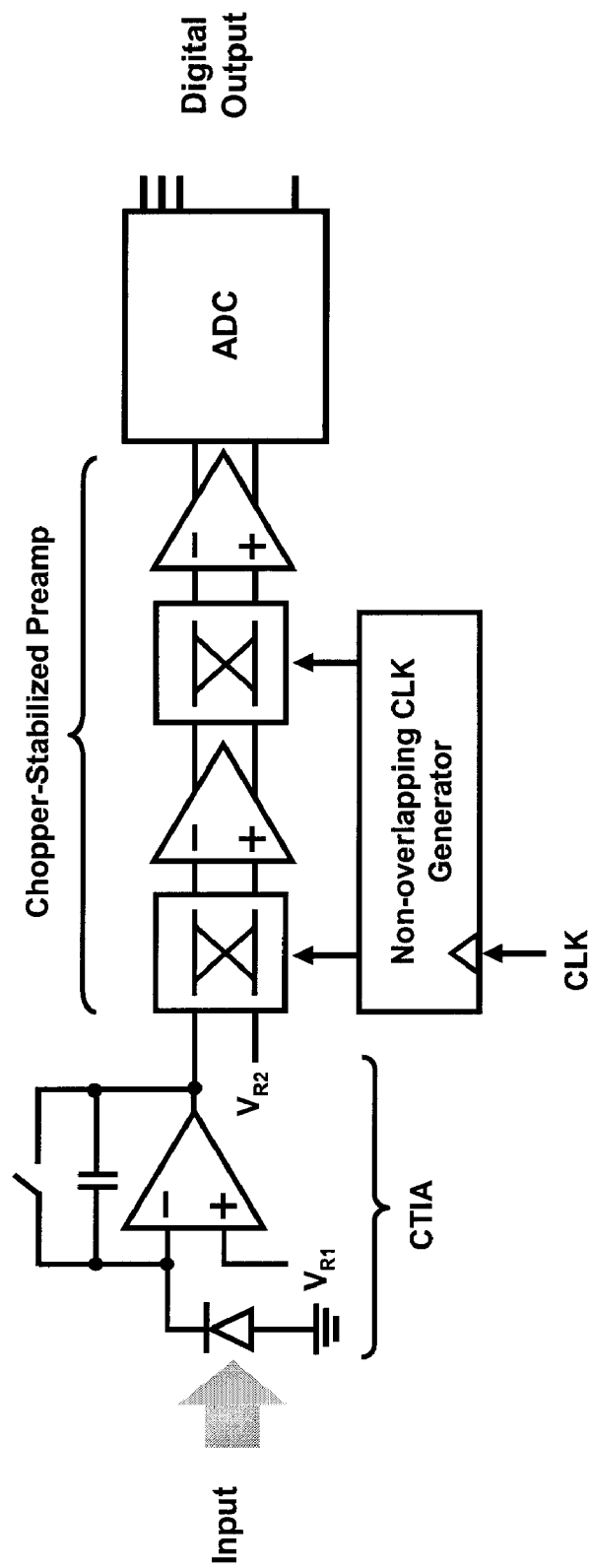
FIG. 10 demonstrates an example design of a system of the invention comprising a capacitive transimpedance amplifier (CTIA).

Most of the CMOS image sensors use direction integration, where the photocurrent is directly integrated over a reverse bias photodiode capacitor. In the design, a capacitive transimpedance amplifier (CTIA) in the pixel is used as a photocurrent integrator. Comparing with a CTIA, a direct integrator suffers from the junction capacitance variation as the reverse bias voltage changes depending on the output signal level. A CTIA does not have any such problems since the photodiode bias is regulated by an operational transimpedance amplifier (OTA) used in the CTIA and it is set to VR1 as shown in FIG. 10. Photocurrent input in the system is integrated using the feedback capacitor.

In order to take full advantage of integration capability of CMOS, an ADC is also included in the pixel level. Pixel level processing relaxes the speed requirement of ADC while removing all analog signal bus lines in the array and significantly reduces the cross-talk issues. To suppress the low frequency noise of the comparator, a chopper stabilized preamplifier has been implemented with overall voltage gain of approximately 60 dBgain.

A measurement of the concentration of Cy3 fluorophores on the surface of the chip using our integrated microarray system can be performed to determine the performance compatibility of this system with fluorescent-based microarrays.

Figure 11:
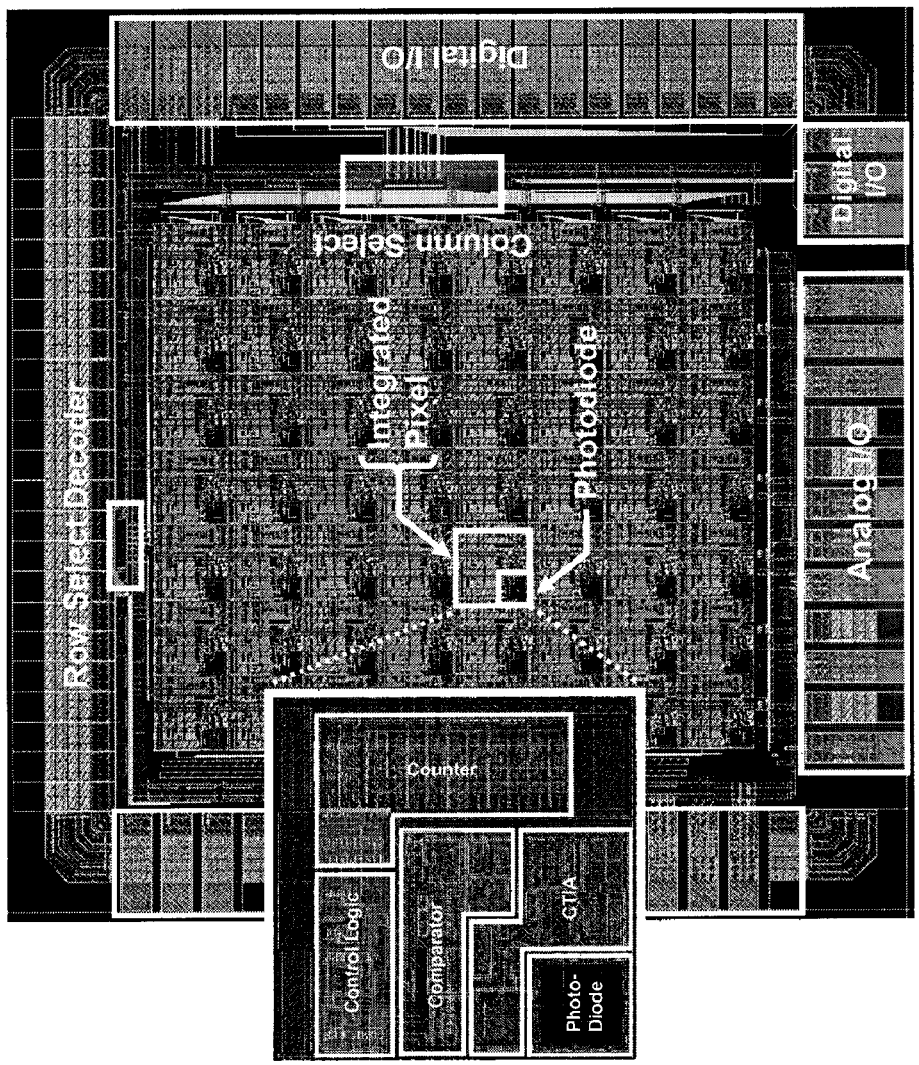
FIG. 11 shows the die photo and the I/O pin allocation of an integrated 7 by 8 pixel bio sensor array.

FIG. 11 shows the die photo and the I/O pin allocation of the integrated 7 by 8 pixel biosensor array. Auxiliary circuits beside the biosensor array include row and column decoder and column switches which are necessary for the functionality of the array.

What is claimed is:

1. An integrated biosensor array, comprising, in order,
   a molecular recognition layer,
   an optical layer, and
   a sensor layer integrated in a sandwich configuration, wherein:
   (a) the molecular recognition layer comprises a plurality of different probes attached at different independently addressable locations, each of said independently addressable locations configured to receive an excitation photon flux directly from a single source located on a single side of said molecular recognition layer, wherein the molecular recognition layer transmits light to the optical layer;
   (b) the optical layer comprises an optical filter layer, wherein the optical layer transmits light from the molecular recognition layer to the sensor layer, whereby the transmitted light is filtered; and
   (c) the sensor layer comprises an array of optical sensors that detect the filtered light transmitted through the optical layer, said sensor layer comprising sensor elements fabricated using a CMOS fabrication process; wherein said molecular recognition layer, said optical layer and said sensor layer comprise an integrated structure in which said molecular layer is in contact with said optical layer and said optical layer is in contact with said sensor layer.

2. The biosensor array of claim 1 wherein the optical layer further comprises an optical coupling layer between the optical filter layer and the molecular recognition layer.

3. The biosensor array of claim 2 wherein the optical coupling layer comprises a plurality of optical waveguides.

4. The biosensor array of claim 2 wherein the optical coupling layer comprises a fiber-optic faceplate.

5. The biosensor array of claim 1 wherein the optical layer is 2 µm to 20 cm thick.

6. The biosensor array of claim 1 wherein the optical layer is 5 µm to 1 cm thick.

7. The biosensor array of claim 1 wherein the optical layer provides thermal insulation between the array of optical sensors and the molecular recognition layer.

8. The biosensor array of claim 1 wherein the sensor layer comprises a photodiode array.

9. The biosensor array of claim 1 wherein the sensor layer comprises embedded detection circuitry connected to the optical sensors.

10. The biosensor array of claim 1 wherein the sensor layer comprises embedded detection and signal processing circuitry connected to the optical sensors.

11. The biosensor array of claim 1, wherein the integrated biosensor array comprises a digital signal processor.

12. The biosensor array of claim 1, wherein the integrated biosensor array comprises an integrated in-pixel photocurrent detector.

13. The biosensor array of 12 wherein the integrated in-pixel photocurrent detector comprises a capacitive transimpedance amplifier (CTIA).

14. The biosensor array of claim 1, wherein the integrated biosensor array has an in-pixel analog to digital converter.

15. The biosensor array of claim 1 wherein the optical filter layer comprises a multilayer dielectric.

16. The biosensor array of claim 15 wherein the optical filter layer has a passband or a stopband with a bandwidth of about 10 nm to 20 nm.

17. The biosensor array of claim 16 wherein the passband or stopband is in the range of 400 nm to 800 nm.

18. The biosensor array of claim 1 wherein the optical filter layer attenuates fluorescent excitation light by $10^2$ to $10^7$.

19. The biosensor array of claim 1 wherein the optical filter layer attenuates fluorescent excitation light by $10^3$ to $10^5$.

20. The biosensor array of claim 1 wherein at least one optical sensor corresponds to one independently addressable location comprising a probe.

21. The biosensor array of claim 1 wherein more than one optical sensor corresponds to one independently addressable location.

22. The biosensor array of claim 1 wherein about 10 to about 1000 optical sensors correspond to one independently addressable location.

23. The biosensor array of claim 1 wherein different optical sensors corresponding to one independently addressable location measure different wavelengths of light.

24. The biosensor array of claim 1 wherein the molecular recognition layer comprises 2 to 1,000,000 probes.

25. The biosensor array of claim 1 wherein the independently addressable locations comprise probes comprising fluorescent moieties.

26. The biosensor array of claim 25 wherein the fluorescent moieties are capable of being quenched upon binding of an analyte comprising a quencher.

27. The biosensor array of claim 25 wherein the fluorescent moieties are bound to the probes.

28. The biosensor array of claim 25 wherein the fluorescent moieties are bound to the surface of the array, but are not covalently bound to the probes.

29. The biosensor array of claim 1 wherein the probes comprise nucleic acids.

30. The biosensor array of claim 1 wherein the probes comprise proteins.

* * * * *